US012595371B2

(12) United States Patent
Buch et al.

(10) Patent No.: US 12,595,371 B2
(45) **Date of Patent: *Apr. 7, 2026**

(54) CONTACT LENS WITH IMPROVED VISION BREAK-UP TIME

(71) Applicant: Johnson & Johnson Vision Care, Inc., Jacksonville, FL (US)

(72) Inventors: John R. Buch, Jacksonville, FL (US); Jie Xu, St. Johns, FL (US); Patricia Martin, Jacksonville, FL (US); Shivkumar Mahadevan, Jacksonville, FL (US); Dawn D. Wright, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 582 days.

This patent is subject to a terminal disclaimer.

(21) Appl. No.: 17/936,914

(22) Filed: Sep. 30, 2022

(65) Prior Publication Data

US 2023/0085695 A1 Mar. 23, 2023

Related U.S. Application Data

(63) Continuation-in-part of application No. 17/110,443, filed on Dec. 3, 2020, now Pat. No. 11,820,899, and (Continued)

(51) Int. Cl.
*C09B 62/465* (2006.01)
*A61L 27/00* (2006.01)
(Continued)

(52) U.S. Cl.
CPC ............ *C09B 62/465* (2013.01); *A61L 27/00* (2013.01); *C08F 230/08* (2013.01); *C08L 77/00* (2013.01);
(Continued)

(58) Field of Classification Search
CPC ..................................................... G02B 1/043
See application file for complete search history.

(56) References Cited

U.S. PATENT DOCUMENTS 3,196,150 A 7/1965 Martin
3,376,303 A 4/1968 Otto et al.
(Continued)

FOREIGN PATENT DOCUMENTS

CN 203965745 U 11/2014
CN 106349212 A 1/2017
(Continued)

OTHER PUBLICATIONS

PCT International Preliminary Report on Patentability, dated Jun. 13, 2023, for PCT Int'l Appln. No. PCT/IB2021/061175.
(Continued)

*Primary Examiner* — Michael F Pepitone
(74) *Attorney, Agent, or Firm* — Raef M. Shaltout

(57) ABSTRACT

Described are polymerizable high energy light absorbing compounds. The compounds absorb various wavelengths of ultraviolet and/or high energy visible light and are suitable for incorporation in various products, such as biomedical devices and ophthalmic devices. Such devices exhibit a number of desirable properties, including favorable vision break-up times.

13 Claims, 3 Drawing Sheets

UV-VIS Transmission Spectrum of Silicone Hydrogel Contact Lenses 4A and 4B

Related U.S. Application Data a continuation-in-part of application No. 16/938,117, filed on Jul. 24, 2020, said application No. 17/110,443 is a continuation of application No. 16/268,897, filed on Feb. 6, 2019, now Pat. No. 10,935,695.

(60) Provisional application No. 62/893,996, filed on Aug. 30, 2019, provisional application No. 62/691,112, filed on Jun. 28, 2018, provisional application No. 62/637,505, filed on Mar. 2, 2018.

(51) Int. Cl.

| | |
|---|---|
| ***C08F 230/08*** | (2006.01) |
| ***C08K 5/1545*** | (2006.01) |
| ***C08K 5/45*** | (2006.01) |
| ***C08L 77/00*** | (2006.01) |
| ***C08L 83/04*** | (2006.01) |
| ***G02B 1/04*** | (2006.01) |
| ***G02C 7/04*** | (2006.01) |
| ***G02C 7/10*** | (2006.01) |

(52) U.S. Cl.

CPC ................ *C08L 83/04* (2013.01); *G02B 1/04* (2013.01); *G02B 1/043* (2013.01); *G02C 7/04* (2013.01); *G02C 7/10* (2013.01); *C08K 5/1545* (2013.01); *C08K 5/45* (2013.01)

(56) References Cited

U.S. PATENT DOCUMENTS 3,408,429 A 10/1968 Otto
3,660,545 A 5/1972 Wichterle
3,769,294 A 10/1973 Catino et al.
3,808,178 A 4/1974 Gaylord
4,113,224 A 9/1978 Clark et al.
4,120,570 A 10/1978 Gaylord
4,136,250 A 1/1979 Mueller et al.
4,153,641 A 5/1979 Deichert et al.
4,197,266 A 4/1980 Clark et al.
4,436,887 A 3/1984 Chromecek et al.
4,495,313 A 1/1985 Larsen
4,659,763 A 4/1987 Gallucci et al.
4,659,782 A 4/1987 Spinelli
4,659,783 A 4/1987 Spinelli
4,716,234 A 12/1987 Dunks et al.
4,740,533 A 4/1988 Su et al.
4,889,664 A 12/1989 Kindt-Larsen et al.
4,910,277 A 3/1990 Bambury et al.
4,997,897 A 3/1991 Melpolder
5,006,622 A 4/1991 Kunzler et al.
5,034,461 A 7/1991 Lai et al.
5,039,459 A 8/1991 Kindt-larsen et al.
5,070,215 A 12/1991 Bambury et al.
5,236,969 A 8/1993 Kunzler et al.
5,244,981 A 9/1993 Seidner et al.
5,270,418 A 12/1993 Kunzler et al.
5,298,533 A 3/1994 Nandu et al.
5,314,960 A 5/1994 Spinelli et al.
5,331,067 A 7/1994 Seidner et al.
5,371,147 A 12/1994 Spinelli et al.
5,470,932 A 11/1995 Jinkerson
5,480,927 A 1/1996 Janssen et al.
5,729,322 A 3/1998 Collins et al.
5,760,100 A 6/1998 Nicolson et al.
5,776,999 A 7/1998 Nicolson et al.
5,789,461 A 8/1998 Nicolson et al.
5,824,719 A 10/1998 Kunzler et al.
5,849,811 A 12/1998 Nicolson et al.
5,872,118 A 2/1999 Kelley et al.
5,916,719 A 6/1999 Kim et al.
5,944,853 A 8/1999 Molock et al.
5,945,465 A 8/1999 Ozark et al.
5,962,548 A 10/1999 Vanderlaan et al.
5,965,631 A 10/1999 Nicolson et al.
5,977,219 A 11/1999 Ravichandran et al.
5,998,498 A 12/1999 Vanderlaan et al.
6,020,445 A 2/2000 Vanderlaan et al.
6,022,158 A 2/2000 Nakayama et al.
6,087,415 A 7/2000 Vanderlaan et al.
6,158,862 A 12/2000 Patel et al.
6,166,218 A 12/2000 Ravichandran et al.
6,207,244 B1 3/2001 Hesch
6,244,707 B1 6/2001 Faubl
6,367,929 B1 4/2002 Maiden et al.
6,373,615 B1 4/2002 Mann et al.
6,420,453 B1 7/2002 Bowers et al.
6,423,761 B1 7/2002 Bowers et al.
6,527,977 B2 3/2003 Helber et al.
6,767,979 B1 7/2004 Muir et al.
6,807,745 B2 10/2004 Orton
6,822,016 B2 11/2004 McCabe et al.
6,867,245 B2 3/2005 Iwata et al.
6,918,931 B2 7/2005 Lai et al.
6,943,203 B2 9/2005 Vanderlaan et al.
6,951,894 B1 10/2005 Nicolson et al.
7,033,391 B2 4/2006 Lai et al.
7,052,131 B2 5/2006 McCabe et al.
7,247,692 B2 7/2007 Laredo
7,249,848 B2 7/2007 Laredo et al.
7,276,544 B2 10/2007 Lai et al.
7,396,890 B2 7/2008 Zanini et al.
7,461,937 B2 12/2008 Steffen et al.
7,468,398 B2 12/2008 Nicolson et al.
7,538,146 B2 5/2009 Nicolson et al.
7,553,860 B2 6/2009 Old
7,553,880 B2 6/2009 Nicolson et al.
7,572,841 B2 8/2009 Chen et al.
7,666,921 B2 2/2010 McCabe et al.
7,691,916 B2 4/2010 McCabe et al.
7,691,918 B2 4/2010 Jinkerson et al.
7,728,051 B2 6/2010 Weinschenk, III et al.
7,781,571 B2 8/2010 Weinschenk, III et al.
7,786,185 B2 8/2010 Rathore et al.
7,803,359 B1 9/2010 Jinkerson et al.
7,825,170 B2 11/2010 Steffen et al.
7,915,323 B2 3/2011 Awasthi et al.
7,934,830 B2 5/2011 Blackwell et al.
7,956,131 B2 6/2011 Arnold et al.
7,994,356 B2 8/2011 Awasthi et al.
8,022,158 B2 9/2011 Rathore et al.
8,026,326 B2 9/2011 Benz et al.
8,043,607 B2 10/2011 Jinkerson
8,113,655 B1 2/2012 Tyrin et al.
8,138,290 B2 3/2012 Blackwell et al.
8,153,703 B2 4/2012 Laredo
8,163,206 B2 4/2012 Chang et al.
8,207,244 B2 6/2012 Laredo
8,236,053 B1 8/2012 Freeman
8,262,947 B2 9/2012 Laredo
8,262,948 B2 9/2012 Laredo et al.
8,273,802 B2 9/2012 Laredo et al.
8,323,631 B2 12/2012 Jinkerson
8,329,775 B2 12/2012 Laredo
8,360,574 B2 1/2013 Ishak et al.
8,389,597 B2 3/2013 Blackwell et al.
8,399,538 B2 3/2013 Steffen et al.
8,415,404 B2 4/2013 Nicolson et al.
8,420,711 B2 4/2013 Awasthi et al.
8,450,387 B2 5/2013 McCabe et al.
8,470,906 B2 6/2013 Rathore et al.
8,476,390 B2 7/2013 Benz et al.
8,487,058 B2 7/2013 Liu et al.
8,507,577 B2 8/2013 Zanini et al.
8,568,626 B2 10/2013 Nicolson et al.
8,585,938 B1 11/2013 Jinkerson et al.
8,618,323 B2 12/2013 Benz et al.
8,637,621 B2 1/2014 Iwata et al.
8,697,770 B2 4/2014 Duis et al.
8,703,891 B2 4/2014 Broad
8,784,867 B2 7/2014 Samuel et al.
8,807,745 B2 8/2014 Nunez et al.
8,940,812 B2 1/2015 Reboul et al.

(56) References Cited

U.S. PATENT DOCUMENTS 8,980,972 B2 3/2015 Driver
9,005,700 B2 4/2015 Bothe et al.
9,056,878 B2 6/2015 Fujisawa et al.
9,057,821 B2 6/2015 Broad et al.
9,125,829 B2 9/2015 Bonda et al.
9,145,383 B2 9/2015 Bonda et al.
9,170,349 B2 10/2015 Mahadevan et al.
9,217,813 B2 12/2015 Liu et al.
9,244,196 B2 1/2016 Scales et al.
9,249,249 B2 2/2016 Awasthi et al.
9,260,544 B2 2/2016 Rathore et al.
9,278,949 B2 3/2016 Loccufier
9,297,928 B2 3/2016 Molock et al.
9,297,929 B2 3/2016 Scales et al.
9,315,669 B2 4/2016 Holland et al.
9,611,246 B2 4/2017 Bonda et al.
9,637,444 B2 5/2017 Qian
9,667,800 B2 5/2017 Rodriguez et al.
9,733,493 B2 8/2017 Wooley
9,765,051 B2 9/2017 Bonda et al.
9,867,800 B2 1/2018 Bonda et al.
9,926,289 B2 3/2018 Bonda et al.
9,927,635 B2 3/2018 Ishak et al.
9,957,258 B2 5/2018 Kunimoto et al.
10,113,075 B2 10/2018 Nesvadba et al.
10,254,443 B2 4/2019 Mccabe et al.
10,268,053 B2 4/2019 Holland et al.
10,338,408 B2 7/2019 Bothe et al.
10,597,515 B2 3/2020 Nesvadba et al.
10,935,695 B2 * 3/2021 Mahadevan ............. G02B 1/04
11,401,400 B2 8/2022 Shishino et al.
11,543,683 B2 * 1/2023 Mahadevan .......... C09B 69/109
11,820,899 B2 11/2023 Mahadevan et al.
11,993,037 B1 5/2024 Mahadevan et al.
2002/0042653 A1 4/2002 Copeland et al.
2004/0070726 A1 4/2004 Ishak
2005/0018131 A1 1/2005 Ishak
2005/0055090 A1 3/2005 Lai et al.
2005/0055091 A1 3/2005 Lai et al.
2005/0243272 A1 * 11/2005 Mainster ............... A61F 2/1659
351/159.24
2005/0254003 A1 11/2005 Jani et al.
2006/0092374 A1 5/2006 Ishak
2006/0252850 A1 11/2006 Jani et al.
2007/0092830 A1 4/2007 Lai et al.
2007/0092831 A1 4/2007 Lai et al.
2007/0100018 A1 5/2007 Hagting et al.
2007/0216861 A1 9/2007 Ishak et al.
2008/0002147 A1 1/2008 Haywood et al.
2008/0221674 A1 9/2008 Blum et al.
2010/0048847 A1 2/2010 Broad
2010/0113641 A1 5/2010 Laredo
2010/0168359 A1 7/2010 Domschke et al.
2010/0321632 A1 12/2010 Sanger
2011/0245818 A1 10/2011 Weinschenk, III et al.
2011/0249234 A1 10/2011 Duis et al.
2012/0010703 A1 1/2012 Paul et al.
2012/0053313 A1 3/2012 Higgs et al.
2012/0196951 A1 8/2012 Mentak
2012/0262792 A1 10/2012 Goldberg et al.
2013/0009059 A1 1/2013 Caruso
2013/0057824 A1 3/2013 Harding et al.
2013/0095235 A1 4/2013 Bothe et al.
2013/0158150 A1 6/2013 Zhang et al.
2013/0168617 A1 7/2013 Alli et al.
2013/0172440 A1 7/2013 Alli et al.
2013/0217620 A1 8/2013 Alli et al.
2014/0024791 A1 1/2014 Alli et al.
2014/0031447 A1 1/2014 Alli et al.
2014/0044654 A1 2/2014 Bonda et al.
2014/0050681 A1 2/2014 Bonda et al.
2014/0093661 A1 4/2014 Trajkovska et al.
2014/0178595 A1 6/2014 Bothe et al.
2014/0300857 A1 10/2014 Cohen-tannoudji et al.
2015/0092155 A1 4/2015 Chang et al.
2015/0094393 A1 * 4/2015 Holland .................. C08L 83/04
522/66
2015/0094395 A1 4/2015 Alli et al.
2015/0164852 A1 6/2015 Bonda et al.
2015/0175732 A1 6/2015 Awasthi et al.
2015/0316688 A1 11/2015 Cefalo et al.
2016/0002200 A1 1/2016 Bonda et al.
2016/0022555 A1 1/2016 Bonda et al.
2016/0170093 A1 6/2016 Laredo et al.
2017/0038605 A1 2/2017 Legerton
2017/0075137 A1 3/2017 Lin et al.
2017/0131574 A1 5/2017 Lee
2017/0184878 A1 6/2017 Duis et al.
2017/0227790 A1 8/2017 Lin et al.
2017/0261768 A1 9/2017 Ambler et al.
2018/0037690 A1 2/2018 Aitken et al.
2018/0164608 A1 6/2018 Schmeder et al.
2018/0208583 A1 7/2018 Kunimoto et al.
2018/0263951 A1 9/2018 Bonda et al.
2018/0371139 A1 12/2018 Mahadevan et al.
2019/0002415 A1 1/2019 Mahadevan et al.
2019/0002459 A1 1/2019 Mahadevan et al.
2019/0121162 A1 4/2019 Alli et al.
2019/0169438 A1 6/2019 Fromentin et al.
2019/0179170 A1 6/2019 Chang et al.
2019/0271798 A1 9/2019 Mahadevan et al.
2019/0271861 A1 9/2019 Hose
2020/0347166 A1 11/2020 Alli et al.
2020/0347167 A1 11/2020 Alli et al.
2020/0399429 A1 12/2020 Alli et al.
2020/0407324 A1 12/2020 Mahadevan et al.
2020/0407337 A1 12/2020 Mahadevan
2021/0061934 A1 3/2021 Martin et al.
2022/0194944 A1 6/2022 Mahadevan
2022/0340759 A1 10/2022 Riederer et al.
2022/0340760 A1 10/2022 Nankivil et al.
2023/0066936 A1 3/2023 Buch et al.
2023/0117655 A1 4/2023 Mahadevan et al.
2023/0288728 A1 9/2023 Mahadevan et al.
2023/0296807 A1 9/2023 Aitken et al.

FOREIGN PATENT DOCUMENTS

CN 106366241 A 2/2017
CN 108586289 A 9/2018
EP 0080539 B1 5/1986
EP 0131468 B1 1/1990
EP 0924203 A1 6/1999
EP 1870735 A1 12/2007
EP 2123638 A1 11/2009
EP 3419961 A1 1/2019
EP 3052534 B1 5/2019
EP 3419961 B1 9/2020
GB 217810 A 6/1924
GB 2319035 A 5/1998
JP H0743918 A 2/1995
JP 2004243596 A 9/2004
JP 2004277581 A 10/2004
JP 2008050463 A 3/2008
JP 4627009 B2 11/2010
JP 2011219512 A 11/2011
JP 5544017 B2 5/2014
JP 2016133593 A 7/2016
RU 2175321 C2 10/2001
RU 2196557 C2 1/2003
RU 2197907 C2 2/2003
RU 2294132 C2 2/2007
RU 2466173 C1 11/2012
RU 2481606 C1 5/2013
RU 2540655 C2 2/2015
RU 2557993 C1 7/2015
RU 2628462 C2 8/2017
WO 9963366 A1 12/1999
WO 0130866 A1 5/2001
WO 0212205 A1 2/2002
WO 0242281 A1 5/2002
WO 2003022321 A2 3/2003
WO 03089519 A1 10/2003
WO 2007050395 A2 5/2007

(56) References Cited

FOREIGN PATENT DOCUMENTS

| | | | |
|---|---|---|---|
| WO | 2008061992 | A2 | 5/2008 |
| WO | 2011130139 | A1 | 10/2011 |
| WO | 2013055746 | A1 | 4/2013 |
| WO | 2013188825 | A1 | 12/2013 |
| WO | 2014018208 | A1 | 1/2014 |
| WO | 2014025370 | A1 | 2/2014 |
| WO | 2014026151 | A1 | 2/2014 |
| WO | 2015048035 | A1 | 4/2015 |
| WO | 2015155748 | A1 | 10/2015 |
| WO | 2016100457 | A1 | 6/2016 |
| WO | 2016175619 | A1 | 11/2016 |
| WO | 2017073467 | A1 | 5/2017 |
| WO | 2017106322 | A1 | 6/2017 |
| WO | 2019166971 | A1 | 9/2019 |
| WO | 2020177534 | A1 | 9/2020 |
| WO | 2020261091 | A1 | 12/2020 |

OTHER PUBLICATIONS

"Compendium of Polymer Terminology and Nomenclature: IUPAC Recommendations", edited by: Richard G. Jones, Jaroslav Kahovec, Robert Stepto, Edward S. Walks, Michael Hess, Tatsuki Kitayama, and W. Val Metanomski., 2008.

"International Preliminary Report on Patentability Received for PCT Appin. No PCT/IB2020/055485", Mailed Date: Dec. 28, 2021, 8 Pages.

"International Preliminary Report on Patentability Received for PCT Appin. No. PCT/IB2020/057732", Mailed Date: Mar. 1, 2022, 8 Pages.

"International Preliminary Report on Patentability Received for PCT Appin. No. PCT/IB2020/057733", Mailed Date: Mar. 1, 2022, 9 Pages.

"International Search Report Received for PCT Appin. No. PCT/IB2019/051582", Mailed date May 24, 2019, 18 pages.

"International Search Report Received for PCT Appin. No. PCT/IB2020/057733", Mailed date Oct. 9, 2020, 16 Pages.

"International Search Report Received for PCT Appin. No. PCT/IB2021/061175", Mailed date Mar. 1, 2022, 15 Pages.

"Statement on Ocular Ultraviolet Radiation Hazards in Sunlight", American Optometric Association, Nov. 10, 1993.

Beatty et al., "Macular pigment and age related macular degeneration", Br. J. Ophthalmol. 1999, vol. 83, pp. 867-877.

Belusa, J. et al., "2-(2-Hydroxyphenyl)benzotriazoles. I. Synthesis and Their Ultraviolet And Infrared Spectra", In Chem.Zvesti, vol. 28, No. 5, pp. 673-679, 1974.

Bernstein et al., "Lutein, zeaxanthin, and meso-zeaxanthin: The basic and clinical science underlying carotenoid-based nutritional interventions against ocular disease", Progress in Retinal and Eye Research, vol. 50, pp. 34-66, (2016).

Berthon, et al., "Synthesis, Electrochemical and Spectroscopic Properties of Pendant Hydroquinone-and Quinone-Substitued Polypyridyl Ruthenium(II) Complexes", In Inorganica Himica Acta, vol. 204, pp. 3-7 , 1993.

Bondyreva E. Y., "Polimerization", Methodological Guidelines for Independent Work, Nizhnekamsk Chemical and Technological Institute of the Federal State Budget Educational Institution of Higher Professional Education, Kazan National Research Technological University, Nizhnekamsk, 2014, pp. 4-13.

Boon et al., "Factors Influencing the Chemical Stability of Carotenoids in Foods", Critical Reviews in Food Science and Nutrition, vol. 50, pp. 515-532 (2010).

Burton et al., "B-Carotene autoxidation: oxygen copolymerization, non-vitamin A products, and immunological activity", Can. J. Chem., vol. 92, pp. 305-316 (2014).

Chakrabarti et al., "Statistics of Real-World Hyperspectral Images", CVPR 2011, pp. 193-200, Jun. 20-25, 2011.

Chen et al., "Dicyanomethylenated Acridone Based Crystals: Torsional Vibration Confinement Induced Emission with Supramolecular Structure Dependent and Stimuli Responsive Characteristics", The Journal of Physical Chemistry, 2016, 587-597, 120.

Crivello, et al., "Photoinitiators for Free Radical Cationic and Anionic Photopolymerisation", In 2nd Edition, John Wiley and Sons, New York, vol. III, pp. 275-298, 1998.

Das, et al., "In vitro and schematic model eye assessment of glare or positive dysphotopsia-type photic phenomena: comparison of a new material IOL to other monofocal IOLs", Journal of Cataract & Refractive Surgery, vol. 45, Issue 2, pp. 219-227, Feb. 2019.

Doutch, et al., "Ultraviolet Light Transmission through the Human Corneal Stroma is Reduced in the Periphery", In Biophysical Journal, vol. 102, No. 6, pp. 1258-1264, Mar. 2012.

Elsherif et al., "Contact Lenses for Color Vision Deficiency", Advanced Materials Technologies, vol. 6, Issue 1, pp. 1-9, Jan. 2021.

Foster et al., "Frequency of Metamerism in Natural Scenes", Journal of the Optical Society of America A, vol. 23, No. 10, pp. 2359-2372, Oct. 2006.

Hafez, et al., "Carbonyl and Thiocarbonyl Compounds. V. Synthesis of Newer Unsaturated Nitriles, Carboxylic Acids, and Esters Derived from Xanthene and Thiaxanthene", In Journal of Organic Chemistry, vol. 26, pp. 3988-3991, Oct. 1961.

Ham, et al., "Retinal Sensitivity to Damage from Short Wavelength Light", In Nature, vol. 260, pp. 153-155, 1976.

Hammond et al., "Contralateral comparison of blue-filtering and non-blue-filtering intraocular lenses: glare disability, heterochromatic contrast, and photostress recovery", Clinical Ophthalmology, 2010, pp. 1465-1473, vol. 4, Dovepress, US.

Harris et al., "Effect of Tinted Contact Lenses on Color Vision", Am J Optom Physiol Opt., vol. 53, No. 3, pp. 145-148, Mar. 1976.

International Conference on Harmonisation (ICH) of Technical Requirements for Registration of Pharmaceuticals for Human Use guideline, Q1B Photostability Testing of New Drug Substances and Products, published on Nov. 1996.

International Preliminary Report on Patentability Received for PCT Appin. No PCT/IB2020/055868, Mailed Date: Dec. 28, 2021, 9 Pages.

International Search Report Received for PCT Appin. No. PCT/IB2020/055485, Mailed date Jul. 23, 2020, 16 Pages.

International Search Report Received for PCT Appln. No. PCT/IB2020/057732, Mailed date Oct. 9, 2020, 15 Pages.

Jockusch, et al., "Photostabilization of Endogenous Porphyrins: Excited State Quenching by Fused Ring Cyanoacrylates", In Photchemical and Photobiological Sciences, vol. 13, No. 8, pp. 1180-1184, 2014.

Johnston et al., "Biologically Active Polymers from Spontaneous Carotenoid Oxidation: A New Frontier in Carotenoid Activity", Plos One, vol. 9, Issue 10, pp. 1-10 (Oct. 2014).

Kolpashchikova, et al., "Organic Chemistry" Part II. Arenes. Halogened Hydrocarbons, Ministry of Education of the Russian Federation, Yaroslavl State Technical University, 3 Pages, 1999.

Lam, et al., "Synthesis of Dinucleating Phenanthroline-Based Ligands", Tetrahedron, vol. 55 Issue 28, pp. 8377-8384, Jul. 9, 1999.

Latif, et al. "Cleavage of Xanthene Ethers: A New Route to 9-Substituted Xanthenes", In Canadian Journal of Chemistry, vol. 42, pp. 1736-1740, 1964.

Laxer, "Soft Tinted Contact Lenses and Color Discrimination", International Contact Lens Clinic, vol. 17, pp. 88-91, Mar.-Apr. 1990.

Luning, et al., "Bimacrocylic 1,10-Phenanthroline Cyclophanes", In Chemischi Beri, vol. 123, Issue 3, pp. 643-645, 1990.

MaCleod et al., "Chromaticity Diagram Showing Cone Excitation by Stimuli of Equal Luminance", Journal of the Optical Society of America, vol. 69, Issue 8, pp. 1183-1186, Aug. 1979.

Mencucci et al., "Visual Outcome, Optical Quality and Patients' Satisfaction with a New Monofocal Intraocular Lens, Enhanced for Intermediate Vision: Preliminary Results", Journal of Cataract & Refractive Surgery, vol. 46, Issue 3, pp. 378-387, Mar. 2020.

Miao et al., "Objective Optical Quality and Intraocular Scattering in Myopic Adults", Investigative Ophthalmology and Visual Science, vol. 55, No. 9, pp. 5582-5587, Sep. 2014.

(56) References Cited

OTHER PUBLICATIONS

Mostafa et al., "The Effect of Age and Gender on Tear Film Breakup Time", In Egyptian Journal of Medical Research, vol. 2, Issue 2, 11 pages, 2021.
Nascimento et al., "Statistics of Spatial Cone-excitation Ratios in Natural Scenes", Journal of the Optical Society of America A, vol. 19, Issue 8, pp. 1484-1490, Aug. 2002.
Nishino, et al., "Manganese (III)-Mediated Carbon-Carbon Bond Formation in the Reaction of Xanthenes with Active Methylene Compounds", The journal of Organic Chemistry, Jan. 1, 1992, pp. 3551-3557, vol. 57, Issue 13.
Parraga et al., "Color and Luminance Information in Natural Scenes", Journal of the Optical Society of America A, vol. 15, No. 3, pp. 563-569, Mar. 1998.
Patel, et al., "Effect of Visual Display Unit Use on Blink Rate and Tear Stability", In Optom Visual Sci, vol. 68, Issue 11, pp. 888-892, 1991.
PCT International Preliminary Report on Patentability, dated Sep. 8, 2020, for PCT Int'l Appln. No. PCT/IB2019/051582.
PCT International Search Report, dated Sep. 23, 2020, for PCT Int'l Appln. No. PCT/IB2020/055868.
Pokorny et al., "Aging of the Human Lens", Applied Optics, vol. 26, No. 8, pp. 1437-1440, Apr. 1987.
Reck, et al., "Enantiopure Chiral Chiral Concave 1,10-Phenanthrolines", In European Journal of Organic Chemistry, vol. 2016, Issue 6, pp. 1119-1131, 2016.
Ribeiro et al., "Antioxidant and pro-oxidant activities of carotenoids and their oxidation products", Food and Chemical Toxicology, vol. 120, pp. 681-699 (2018).
Sato, et al., "Synthesis and Characterization of Electron Transporting Polymers having Thioxanthene Derivatives", In Synthetic Metals, vol. 105, pp. 55-60, Jan. 1, 1999.
Selvam, et al., "Tunable anchoring groups@acridone-linked triphenylamine based pendant chromophores and their effects on the photovoltaic performance as sensitizers for dye-sensitized solar cells", RSC Advances, vol. 6 Issue 110, pp. 109054-109060, 2016.
Stockman et al., "The Spectral Sensitivities of the Middle- and Long-wavelength-sensitive Cones Derived from Measurements in Observers of Known Genotype", Vision Research, vol. 40, pp. 1711-1737, 2000.
Stringham et al., "Macular Pigment and Visual Performance in Glare: Benefits for Photostress Recovery, Disability Glare, and Visual Discomfort", IOVS, Sep. 2011, vol. 52, No. 10, pp. 7406-7415.
Sutyagin et al., "Chemistry and Physics of Polymers", In Training Manual, TPU Publishing House, Tomsk, Chapter 1, Chapter 2, 40 pages, 2003.
Takeda et al., "Anisotropic Dissociation of TT-TT Stacking and Flipping-Motion-Induced Crystal Jumping in Alkylacridones and Their Dicyanomethylene Derivatives", Chem. Eur. J., 2016, 7763-7770, 22.
Tan, et al., "Dynamic Change of Optical Quality in Patients with Dry Eye Disease", In Invest Ophthalmol Vis Sci. vol. 56, Issue 5, pp. 2848-2854, May 2015.
Tester, et al., "Dysphotopsia in phakic and pseudophakic patients: incidence and relation to intraocular lens type", In Journal of Cataract & Refractive Surgery, vol. 26, Issue 6 ,pp. 810-816, Jun. 2000.
Tsubota, et al., "Dry Eyes and Video Display Terminals", In New England Journal of Medicine, vol. 328, Issue 8, p. 584, Feb. 25, 1993.
Ty et al., "Oxidation and Thermal Degradation of Carotenoids", Journal of Oil Palm Research, vol. II, No. 1, pp. 62-78 (Jun. 1999).
Van den Berg, T. J. T. P., "Importance of Pathological Intraocular Light Scatter for Visual Disability", In Documenta Ophthalmologica, vol. 61, pp. 327-333, 1986.
Xi et al., "Assessment of Tear Film Optical Quality in a Young Short Tear Break-up Time Dry Eye: Case-control study", Medicine, vol. 98, Issue 40, pp. 1-6, 2019.
Belikov, V.G., "The Relationship Between Chemical Structure, Properties of Substances and Their Effect on the Organism", Pharmaceutical Chemistry, pp. 27-29, 2007.
Dyson et al., "Chemistry of Synthetic Drugs Substances", Moscow: Mir, 18 pages, 1964.
Fadli et al., "Permeation and Pervaporation of Water through Contact Lens Materials", Johnson & Johnson Vision Care, Inc. Jacksonville, FL, USA, 1 page, 2016.
International Search Report and Written Opinion, received for PCT Application No. PCT/IB2018/053669, mailed on Jul. 17, 2018, 14 pages.
International Search Report and Written Opinion, received for PCT Application No. PCT/IB2018/054585, mailed on Nov. 9, 2018, 12 pages.
International Search Report and Written Opinion, received for PCT Application No. PCT/IB2018/054588, mailed on Oct. 4, 2018, 17 pages.
International Search Report and Written Opinion, received for PCT Application No. PCT/IB2023/055938, mailed on Oct. 18, 2023, 12 pages.
ISO 18369-3, "Ophthalmic Optics-Contact lenses", Measurement methods, Part 3, 44 pages, Aug. 15, 2006.
ISO 18369-4, "Ophthalmic Optics-Contact Lenses-Part 4: Physicochemical Properties of Contact Lens Materials", International Organization for Standardization, Aug. 15, 2006, 38 pages.
ISO 9913-1, "Optics and Optical Instruments—Contact Lenses—Part 1: Determination of Oxygen Permeability and Transmissibility by the FATT Method", International Organization for Standardization, Nov. 1, 1996, 16 pages.
Riederer et al, "Permeation and Pervaporation of Water through Contact Lens Materials", Johnson & Johnson Vision Care, Inc., 19 pages, Nov. 9-12, 2016.
Riederer et al., "New Methods for Measuring Water Transport through Hydrogel Contact Lenses", Johnson & Johnson Vision, Jacksonville, FL, 1 page, May 7-11, 2017.
Riederer et al., "Pervaporation as a Metric for Evaporative Water Loss from Contact Lenses", Johnson & Johnson Vision Care, Inc., 12 pages, Jun. 2020.
Riederer et al., "Water Loss from Contact Lenses: Material Dependent Rates of Evaporation and Permeation", Johnson & Johnson Vision, 1 page, Jun. 9-11, 2017.
Riederer et al., "Water Loss from Contact Lenses: Material Dependent Rates of Evaporation and Permeation", Johnson & Johnson Vision Care Inc., Florida USA, 5 pages, Dec. 1-2, 2017.
Riederer, Donald, "Evaporation Rates from Hydrogel Contact Lenses Using Dynamic Vapor Sorption", Johnson & Johnson Vision Care, Inc., 48 pages, Sep. 17-18, 2018.
Fletcher et al., "Visibility Through Atmospheric Haze and Its Relation to Macular Pigment", Optometry and Vision Science, vol. 91, No. 09, pp. 1089-1096, 2014.
Hammond et al., "The Influence of Filtering by the Macular Carotenoids on Contrast Sensitivity Measured Under Simulated Blue Haze Conditions", Vision research, vol. 63, pp. 58-62, Jun. 15, 2012.
Kelly, Susan A., "Effect of Yellow-tinted Lenses on Brightness", Journal of the Optical Society of America A, vol. 07, No. 10, pp. 1905-1911, 1990.
Liu, Zhuo., "Tutorial on Modern Rock and Mineral Analytic Experiments", Geological Press, 42 Pages, Oct. 31, 2015.
Wooten et al., "Macular Pigment: Influences on Visual Acuity and Visibility", Progress in Retinal and Eye Research, vol. 21, No. 02, pp. 225-240, Mar. 2002.
Unpublished U.S. Appl. No. 18/871,664, filed Dec. 4, 2024, 103 pages.
Krick et al. "Temperature—DependentDynamics of Push—Pull Rotor SystemsBased on Acridinylidene CyanoaceticEsters", European Journal of Organic Chemistry, pp. 5141-5146, Jul. 26, 2017.
Ma et al., "Studies on K2CO3—Catalyzed 1,4—Addition of 1,2—Allenic Ketones with Diethyl Malonate:Controlled Selective Synthesis of β, γ—Unsaturated Enones and α Pyrones", Journal of Organic Chemistry, vol. 68, pp. 8996-9002, Oct. 24, 2003.

(56) References Cited

OTHER PUBLICATIONS

Maas et al., “Dication Ethers- 10. Stable Dipoles from A Bis-Acridinium Ether Salt and Cyclic Beta-Diketonates”, Tetrahedron, vol. 41, No. 20, pp. 4529-4536, 1985.

* cited by examiner

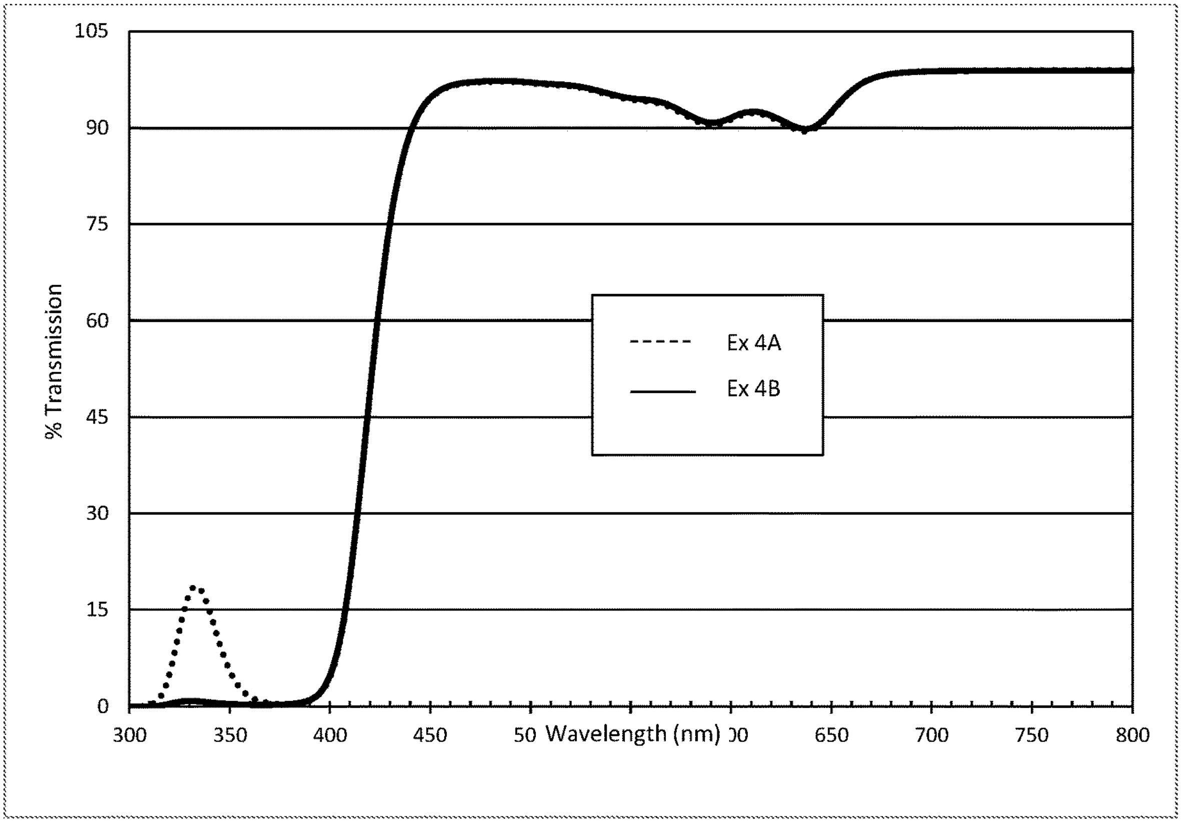
FIG. 1 – UV-VIS Transmission Spectrum of Silicone Hydrogel Contact Lenses 4A and 4B

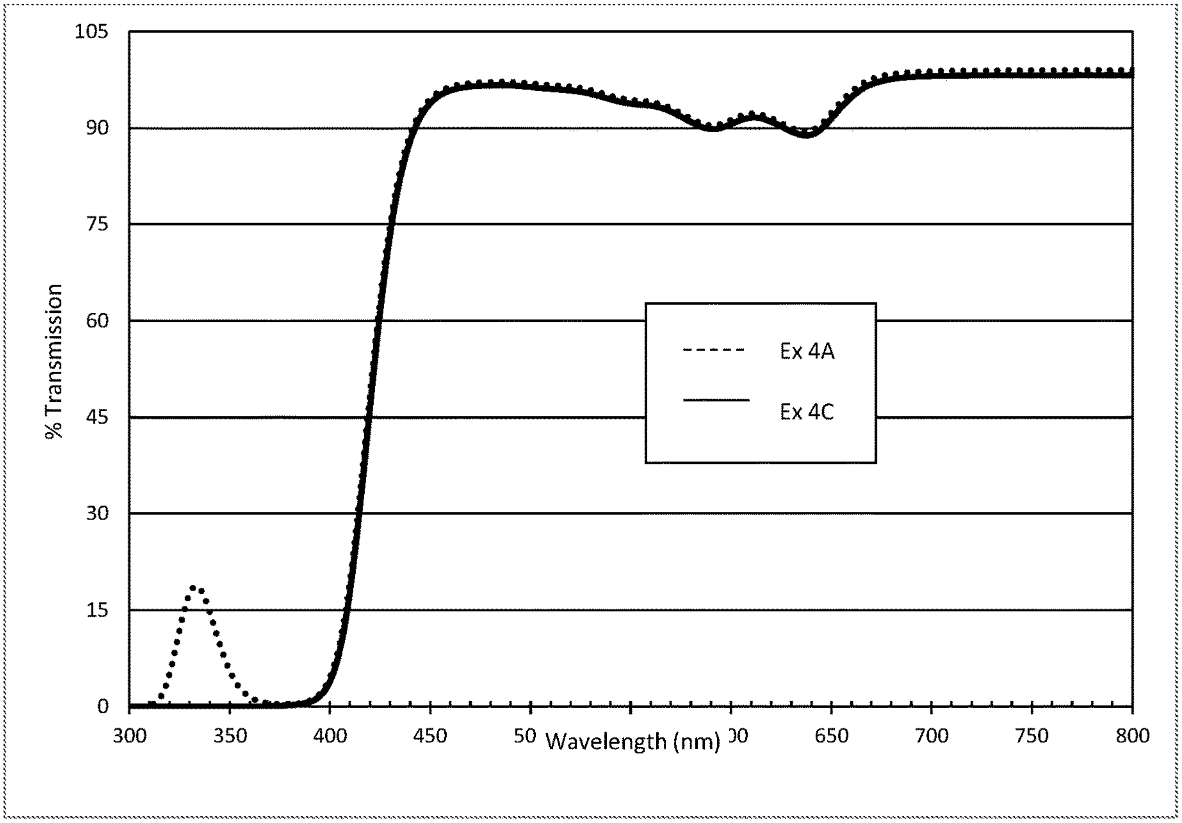
FIG. 2 – UV-VIS Transmission Spectrum of Silicone Hydrogel Contact Lenses 4A and 4C

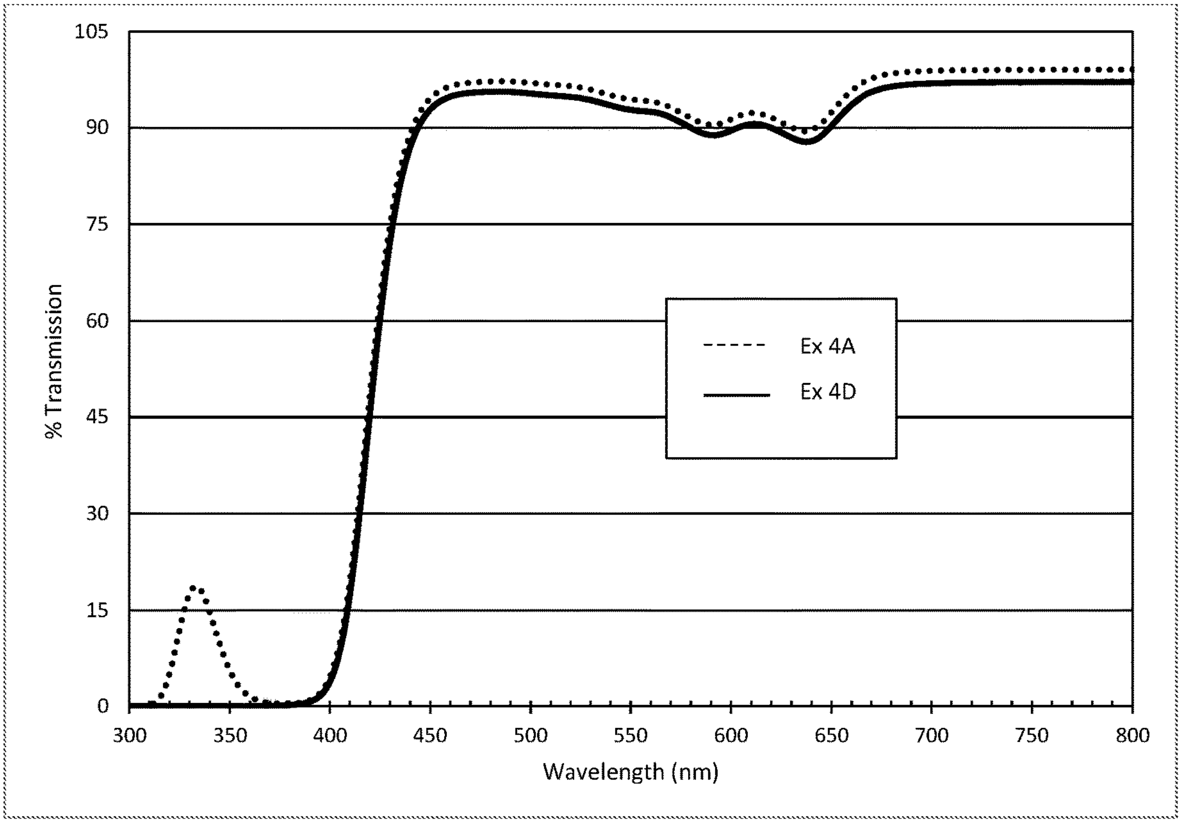
FIG. 3 – UV-VIS Transmission Spectrum of Silicone Hydrogel Contact Lenses 4A and 4D

CONTACT LENS WITH IMPROVED VISION BREAK-UP TIME

RELATED APPLICATIONS

This application is a continuation-in-part of U.S. patent application Ser. No. 16/938,117, filed Jul. 24, 2020, which claims priority to U.S. Provisional Patent Application Ser. No. 62/893,996, filed Aug. 30, 2019, and is a continuation-in-part of U.S. patent application Ser. No. 17/110,443, filed Dec. 3, 2020, now U.S. Pat. No. 11,820,899; which is a continuation of U.S. patent application Ser. No. 16/268,897, filed on Feb. 6, 2019, now U.S. Pat. No. 10,935,695, which claims priority to U.S. Provisional Patent Application Ser. No. 62/691,112, filed Jun. 28, 2018, and U.S. Provisional Patent Application Ser. No. 62/637,505, filed Mar. 2, 2018, each of which is incorporated herein by reference in its entirety.

FIELD OF THE INVENTION

The invention relates to contact lenses that contain high energy visible light absorbing compounds and their use for improving one or more wearer benefits and other properties.

BACKGROUND OF THE INVENTION

High energy light from the sun, such as UV light and high-energy visible light, is known to be responsible for cellular damage. While most of the radiation below 280 nm in wavelength is absorbed by the earth's atmosphere, photons possessing wavelengths ranging between 280 and 400 nm have been associated with several ocular disorders including corneal degenerative changes, and age-related cataract and macular degeneration. (See Statement on Ocular Ultraviolet Radiation Hazards in Sunlight, American Optometric Association, Nov. 10, 1993). The human cornea absorbs some radiation up to 320 nm in wavelength (30% transmission) (Doutch, J. J., Quantock, A. J., Joyce, N.C., Meek, K. M, *Biophys. J,* 2012, 102, 1258-1264), but is inefficient in protecting the back of the eye from radiation ranging from 320 to 400 nm in wavelength.

Contact lens standards define the upper UV radiation wavelength at 380 nm. The current Class I UV absorbing criteria defined by the American Optometric Association require >99% of the radiation between 280 and 315 nm (UV B) and >90% of the 316 to 380 nm (UV A) radiation to be absorbed by the contact lens. While the criteria effectively address protection of the cornea (<1% UV B transmittance), there is little attention paid to the lower energy UV or violet radiation (>380<400 nm) associated with retinal damage (Ham, W. T, Mueller, H. A., Sliney, D. H. *Nature* 1976; 260(5547):153-5) or to HEV radiation.

High energy-visible (HEV) radiation may cause visual discomfort or circadian rhythm disruption. For example, computer and electronic device screens, flat screen televisions, energy efficient lights, and LED lights are known to generate HEV light. Prolonged exposure to such sources of HEV light may cause eye strain. Viewing HEV light emitting devices at night is also postulated to disrupt the natural circadian rhythm leading, for example, to inadequate sleep.

Shorter blue-violet wavelengths are more uncomfortable to view than longer orange-red wavelengths (assuming equal energy output) and scattering within the eye is known to decrease the contrast of objects (Van Den Berg, TJTP, Importance of pathological intraocular light scatter for visual disability, *Documenta Ophthalmologica,* 1986; 61(3-4):327-333). Further, scatter, especially from violet light, is associated with greater halos and starbursts, which are more prevalent at night and may be a significant issue for drivers (Das, K K, Werner, L, Collins, S, Hong X, In vitro and schematic model eye assessment of glare or positive dysphotopsia-type photic phenomena: Comparison of a new material IOL to other monofocal IOLs, *Journal of Cataract and Refractive Surgery,* 2019; 45(2):219-227; Tester, R, Pace, N L, Samore, M, Olson, R J, Dysphotopsia in phakic and pseudophakic patients: incidence and relation to intraocular lens type, *Journal of Cataract and Refractive Surgery,* 2000; 26(6):810-816).

Absorption of high energy light radiation before it reaches the eye therefore continues to be a desirable goal in the ophthalmic field. However, the extent to which a particular wavelength range is absorbed is also important. For instance, in the UV A and UV B ranges, it may be desirable to absorb as much radiation as possible. On the other hand, since HEV light forms a part of the visible spectrum, complete absorption of HEV light may negatively affect vision. With HEV light, therefore, partial absorption may be more desirable.

Human tears are composed of a lipid layer, an aqueous layer, and a mucin layer which together are referred to as the tear film. The tear film is essential to maintaining ocular comfort and visual clarity, with the longer it takes for a person's tear film to break (known as tear break-up time or TBUT) the better. It is known that TBUT declines with age and research shows that TBUT can reduce by 50% by the age of fifty (Mostafa et al., The Effect of Age and Gender on Tear Film Breakup Time. *Egyptian Journal of Medical Research,* 2021; 2:137-148).

Tear film stability can be assessed through both in-vitro and in-vivo methods. In-vivo tests are conducted on human eyes and can be invasive (e.g. with fluorescein) or non-invasive. In-vitro tests are conducted in a laboratory, aiming to replicate the natural environment of the eye. A more clinically relevant in-vivo way to measure tear film stability is to measure non-invasively the time taken for the tear film to break enough to disrupt vision. One such measurement is referred to as vision break-up time (or VBUT), with longer VBUT times being better.

There is a need for materials that provide targeted absorption of undesirable wavelengths of high energy radiation, and that are processable into functional products. Compounds that absorb or attenuate high energy radiation, when used in ophthalmic devices, can help protect the cornea, as well as the interior cells in the ocular environment, from degradation, strain, and/or circadian rhythm disruption. There is also a need for materials that help improve tear film stability and increase the vision break-up time of contact lens wearers.

SUMMARY OF THE INVENTION

The invention relates to contact lenses that contain HEV light filtering compounds and polyamide internal wetting agents such as polyvinylpyrrolidone (PVP). The HEV filtering compounds provide the lenses with targeted absorption of blue light wavelengths. The combination of the polyamide internal wetting agent together with the HEV light filtering compound result in lenses that also exhibit increased vision break-up times when compared to other contact lenses, such as lenses that contain a polyamide internal wetting agent but do not include an HEV light filter.

Accordingly, in one aspect the invention provides a contact lens that is a free radical reaction product of a reactive mixture comprising: one or more monomers suitable for making the contact lens; a high energy visible (HEV) light absorbing compound; and up to eleven weight percent of a polyamide internal wetting agent. The contact lens transmits from 0 percent to 70 percent of light having a wavelength range of 400 to 409 nm. In a population of wearers, wearers of the contact lens are more likely to achieve a vision break-up time of longer than 10 seconds compared to wearers of a control lens that transmits at least 90 percent of light across the wavelength range of 400 to 409 nm (or across the wavelength range of 400 to 450 nm).

In a further aspect, contact lenses are provided in which the HEV light absorbing compound is of formula I:

Formula I

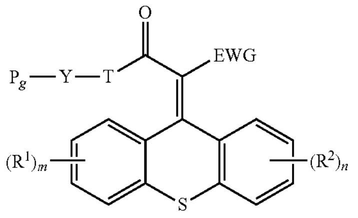

wherein:

- m and n are independently 0, 1, 2, 3, or 4;
- T is a bond, O, or NR;
- Y is a linking group;
- $P_g$ is a polymerizable group;
- R at each occurrence is independently H, $C_1$-$C_6$ alkyl, cycloalkyl, heterocycloalkyl, aryl, heteroaryl, or Y—$P_g$;
- $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
- EWG is an electron withdrawing group, such as cyano, amide, ester, keto, or aldehyde (preferably cyano).

BRIEF DESCRIPTION OF DRAWINGS

FIG. 1 shows UV-VIS transmission spectrum of silicone hydrogel contact lenses of Examples 4A and 4B.

FIG. 2 shows UV-VIS transmission spectrum of silicone hydrogel contact lenses of Examples 4A and 4C.

FIG. 3 shows UV-VIS transmission spectrum of silicone hydrogel contact lenses of Examples 4A and 4D.

DETAILED DESCRIPTION OF THE INVENTION

It is to be understood that the invention is not limited to the details of construction or process steps set forth in the following description. The invention is capable of other embodiments and of being practiced or being carried out in various ways using the teaching herein.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and vertebrates.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495, 313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and, when subjected to polymerization conditions, form the conventional or silicone hydrogels of the present invention as well as contact lenses made therefrom. The reactive monomer mixture may comprise reactive components such as the monomers, macromers, prepolymers, cross-linkers, and initiators, additives such as wetting agents, polymers, dyes, light absorbing compounds such as UV absorbers, pigments, dyes and photochromic compounds, any of which may be reactive or non-reactive but are capable of being retained within the resulting contact lens, as well as pharmaceutical and nutraceutical compounds, and any diluents. It will be appreciated that a wide range of additives may be added based upon the contact lens which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as $—CH_2—$, $—CH_2CH_2—$, $—CH_2CH_2CH_2—$, $—CH_2CH(CH_3)CH_2—$, and $—CH_2CH_2CH_2CH_2—$.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as $—CF_3—$ or $—CF_2CF_3—$. "Haloalkylene" means a divalent haloalkyl group, such as $—CH_2CF_2—$.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as $—CH_2CH_2NH—$.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., $—[Si—O]_n—$, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si—$ and "siloxy" refers to a structure of formula $R_3Si—O—$, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula $-(alkylene-O)_p—$ or $—(O-alkylene)_p-$, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., $HO—[CH_2CH_2O]_p—$ or $CH_3O—[CH_2CH_2O]_p—$). Examples of alkyleneoxy include polyethyleneoxy, polypropyleneoxy, polybutyleneoxy, and poly (ethyleneoxy-co-propyleneoxy).

"Oxaalkylene" refers to an alkylene group as defined above where one or more non-adjacent $CH_2$ groups have been substituted with an oxygen atom, such as $—CH_2CH_2OCH(CH_3)CH_2—$. "Thiaalkylene" refers to an alkylene group as defined above where one or more non-adjacent $CH_2$ groups have been substituted with a sulfur atom, such as $—CH_2CH_2SCH(CH_3)CH_2—$.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester ($—CO_2—$), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., $—OCF_2—$, $—OCF_2CF_2—$, $—OCF_2CH_2—$), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula E below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula E, L and $L^2$ are indicated as both being alkylene-cycloalkylene, then Rg-L is preferably Rg-alkylene-cycloalkylene- and $-L^2$-Rg is preferably -cycloalkylene-alkylene-Rg.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "high energy radiation absorber," "UV/HEV absorber," or "high energy light absorbing compound" refer to chemical materials that absorb various wavelengths of ultraviolet light, high energy visible light, or both. The terms "high energy visible light absorbing compound" or "HEV light absorbing compound" and similar terms refer to chemical materials that absorb one or more wavelengths of high energy visible light, for instance one or more wavelengths in the range of 400 to 450 nm. A material's ability to filter certain wavelengths of light can be determined by measuring its UV/Vis transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. As used herein, unless the context clearly indicates otherwise, if the amount of a contact lens's transmission is indicated as a percentage for a particular wavelength range, it is to be understood that the material exhibits the percent transmission at all wavelengths within that range. On the other hand, reference to an "average transmission" may be calculated as the average of the percent transmission in 1 nm increments over the identified range. For purposes of the invention, a material that has a transmission of 90 percent or greater across the wavelength range of 400 to 450 nm is not an HEV light absorbing material.

The terms "photostable," "photostability," or similar expressions mean that a contact lens (containing an HEV light absorbing compound) doesn't exhibit a substantial change in its visible light transmission spectrum after exposure to light, when packaged in a clear blister pack, under conditions of the International Conference on Harmonisation (ICH) of Technical Requirements for Registration of Pharmaceuticals for Human Use guideline, Q1B Photostability Testing of New Drug Substances and Products, published on November 1996. Preferably, the exposure is conducted under the ICH Photostability Guideline using an Option 2 light source with an estimated illuminance exposure of $1.5192\times10^6$ Lux hours (168.8 hours exposure time) and an estimated ultraviolet irradiation exposure of 259.4 Watt hours/$m^2$ (16.2 hours exposure time), preferably in a photostability chamber that is controlled at 25° C./Amb RH. When lenses are measured within a blister pack, the blister pack is exposed foil side down to maximize irradiance from the light source during photo exposure. After exposure, the UV/Vis spectrum of the test lens is collected and compared to a control lens (a lens that was not subjected to Q1B conditions). Photostability may be represented as the percent change in average transmission of the test lens relative to the control lens at a selected wavelength range. The change may be calculated as the absolute value of the difference in the average transmission (over the selected wavelength range) between the control lens and the test lens, divided by the average transmission of the control lens (at the selected wavelength range). For purposes of this invention, a contact lens is considered to be photostable if the change in average transmission over the selected wavelength range (e.g., 380 to 450 nm) is 20 percent or less, or 15 percent or less, or 10 percent or less, or 7 percent or less, or 5 percent or less, or 2 percent or less. The measurement may, for instance, be made on a −1.00 diopter contact lens.

The term "photochromic compound" refers to a material which reversibly changes its absorption properties (i.e. color) caused by a photochemical reaction within the material upon exposure to specific wavelengths of electromagnetic radiation. By way of example, a photochromic compound may exhibit a reversible change in average transmission of 5% or more, or 10% or more, or 20% percent or more, in the visible portion of the electromagnetic spectrum (e.g., in the wavelength range of about 380 nm to about 760 nm) when exposed to UV or HEV light. A "static compound" is a material that is not photochromic, thus the material does not undergo a photochemical reaction that reversibly changes its color. Preferably, the HEV light absorbing compounds for use in the invention are static compounds.

"Vision break-up time" or "VBUT" represents the point at which a wearer's vision quality drops below a pre-determined threshold as a result of break-up of the tear film. Generally, individual VBUT results in a wearer cohort are recorded for each lens worn and then statistical analysis of all randomized subjects provides the probability of a lens having a VBUT of greater than a specified time, such as 10 seconds. More specifically, VBUT may be determined in a clinical study using a double pass (DP) wave-front sensor such as the HD Analyzer™ instrument (Visiometrics S. L., Terrassa, Spain) as described in the Examples below. Irregularities of the air-tear film interface of the ocular surface contribute to fluctuation of vision in the form of ocular light scatter as measured by the DP imaging system, degrading retinal image quality. The DP system captures dynamic changes of the point spread function (PSF) and calculates the mean value of objective scatter index (OSI) over a defined period of time. Temporal changes of OSI provide a functional analysis of the impact of tear film instability on retinal image quality. The results for VBUT can be categorized to a dichotomous variable (VBUT greater than 10 seconds=1, Others=0) and statistically analyzed using a generalized linear mixed model with a binary distribution and logit as a link function. Statistical superiority is established if the lower bound of the 2-sided 95% Confidence Interval (CI) constructed for the odds ratio (Test over Control) is above 1.0.

Where a lens of the invention is compared to a control lens, the term "control lens" means a contact lens that is substantially identical to the lens of the invention, except that it transmits at least 90 percent of light across the wavelength range of 400 to 409 nm. Thus, the control lens may be manufactured from substantially the same materials as the lens of the invention, but without an HEV light absorbing compound.

"Population of wearers" and related terms mean a group of contact lens wearers that are between 19 and 39 years old, in need of spherical vision correction, but with otherwise healthy eyes. Where a comparison is being made between wearers of a lens of the invention and wearers of a control lens, the population of wearers are represented by participants in a crossover clinical study (i.e., where the invention and control lenses are evaluated on the same participants) as further described in Example 6 below. More specifically, the comparison is between the participants that are the intent-to-treat analysis population, at one week follow-up. The intent-to-treat population means all randomized subjects regardless of actual treatment and subsequent withdrawal from the study or deviation from protocol. The analysis is conducted using an intent-to-treat population of 47 subjects with observed cases only (no missing data imputation).

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

As noted above, the invention provides a contact lens, including a silicone hydrogel contact lens, that is a free radical reaction product of a reactive mixture that includes an HEV light absorbing compound and a polyamide internal wetting agent. The contact lens exhibits certain, desirable, light transmission properties.

For instance, a contact lens of the invention may transmit from 0 percent to 70 percent, or from 0.2 to 70 percent, or from 1 to 70 percent, of light across a wavelength range of 400 to 409 nm. The transmission of the contact lens across the 400 to 409 nm wavelength range may be at least 2 percent, or at least 3 percent, or at least 4 percent. The transmission of the contact lens across the 400 to 409 nm range may be up to 60 percent, or up to 50 percent, or up to 40 percent, or up to 30 percent, or up 20 percent.

The contact lens may transmit 10 percent or less of light across a wavelength range of 200 to 279 nm. The transmission of the contact lens across the 200 to 279 nm wavelength range may be 5 percent or less or 1 percent or less, or less than 1 percent.

The contact lens may transmit 45 percent or less of light across a wavelength range of 280 to 399 nm. The transmission of the contact lens across the 280 to 399 nm wavelength range may be 35 percent or less, or 25 percent or less, or 20 percent or less, or 10 percent or less, or 5 percent or less, or 1 percent or less.

The contact lens may transmit at least 10 percent of light across a wavelength range of 410 to 424 nm. The transmission of the contact lens across the 410 to 424 nm wavelength range may be at least 15 percent. The transmission of the contact lens across the 410 to 424 nm wavelength range may be up to 95 percent, up to 85 percent, up to 75 percent, or up 65 percent.

The contact lens may transmit at least 50 percent of light across a wavelength range of 425 to 449 nm. The transmission of the contact lens across the 425 to 449 nm range may be at least 60 percent.

The contact lens may transmit at least 80 percent of light across a wavelength range of 450 to 800 nm. The transmission of the contact lens across the 450 to 800 nm wavelength range may be at least 85 percent.

The contact lens may transmit from 0 to 70 percent or from 0.2 to 70 percent, or from 1 to 70 percent of light across a wavelength range of 400 to 409 nm; and 45 percent or less of light across a wavelength range of 280 to 399 nm.

The contact lens may transmit from 0 to 70 percent or from 0.2 to 70 percent, or from 1 to 70 percent of light across a wavelength range of 400 to 409 nm; 45 percent or less of light across a wavelength range of 280 to 399 nm; and at least 80 percent of light across a wavelength range of 450 to 800 nm.

The contact lens may transmit from 0 to 70 percent or from 0.2 to 70 percent, or from 1 to 70 percent of light across a wavelength range of 400 to 409 nm; 45 percent or less of light across a wavelength range of 280 to 399 nm; from 10 to 95 percent of light across a wavelength range of 410 to 424 nm; at least 50 percent of light across a wavelength range of 425 to 449 nm; and at least 80 percent of light across a wavelength range of 450 to 800 nm.

In addition to exhibiting desirable light transmission properties, the contact lenses of the invention, including the silicone hydrogel contact lenses, also provide wearers with improved vision break-up times. As shown by the Examples below, it has been discovered that contact lenses that contain an HEV light absorbing compound, in addition to a polyamide internal wetting agent, exhibit a longer VBUT than lenses that contain a polyamide internal wetting agent but do not include an HEV light absorbing compound. Without wishing to be bound by theory, it is believed that the presence of an HEV light absorbing compound in a reactive mixture that also contains a polyamide internal wetting agent results in a distribution of the polyamide internal wetting agent in the lens that is favorable for increasing VBUT. This may be because the HEV light absorbing compound impacts the polymerization process. For instance where the polymerization is initiated with a visible light photoinitiator, the HEV light absorbing compound may absorb some of the visible light that would otherwise activate the photoinitiator, thus affecting the polymerization and consequent morphology of the lens.

The lenses of the invention provide improved VBUT. As indicated above, VBUT represents the point at which a wearer's vision quality drops below a pre-determined threshold as a result of break-up of the tear film, expressed as an odds ratio. In the invention, VBUT values are measured in a clinical study of a population of lens wearers. Further details are provided in the examples.

According to the invention, wearers of the contact lens are more likely to achieve a vision break-up time of longer than 10 seconds compared to wearers of a control lens that transmits at least 90 percent of light across the wavelength range of 400 to 409 nm. Wearers of the contact lens of the invention may be greater than 1.1 times, or greater than 1.2 times, or greater than 1.3 times, or greater than 1.4 times, or greater than 1.5 more likely to achieve a vision break-up time of more than 10 seconds compared to wearers of the control lens. Wearers of the contact lens of the invention may be less than 1.7 times more likely to achieve a vision break-up time of more than 10 seconds compared to wearers of the control lens.

In a further aspect, wearers of the contact lens of the invention can be about 1.6 times more likely to achieve a vision break-up time of longer than 10 seconds compared to wearers of the control lens (based on the estimated odds ratio). The odds ratio of VBUT longer than 10 seconds (invention lens over control lens) is estimated between 1.01 and 2.48 at the 95% confidence level. The VBUT numbers may be determined at 1 week follow-up. Additional details for conducting an appropriate clinical study are provided in Example 6.

Wearers of the contact lens of the invention may exhibit a statistically significant improvement in VBUT compared to wearers of a control lens.

The contact lens of the invention may be a soft hydrogel contact lens, preferably a silicone hydrogel contact lens. The transmission wavelengths and percentages discussed above may be measured on various thicknesses of lenses. For example, the center thickness may be from 70 to 300 microns, or from 80 to 230 microns, or from 80 to 110 microns, or from 90 to 110 microns. The concentration of the HEV light absorbing compounds may be adjusted to achieve the foregoing transmission properties. For instance, the concentration may be in the range of at least 0.01 percent, or at least 0.1 percent, or at least 1 percent, or at least 2 percent; and up to 10 percent or up to 5 percent, based on the weight percentages of all components in the reactive mixture, excluding diluent. A typical concentration may be in the range of 0.2 to 5 percent.

The HEV light absorbing compound for use in the contact lenses of the invention may be a compound of formula I:

Formula I

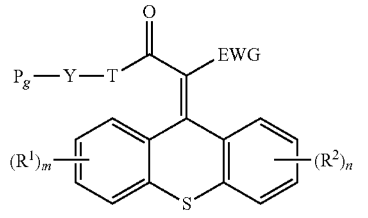

wherein:

m and n are independently 0, 1, 2, 3, or 4;

T is a bond, O, or NR;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$; and $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group, such as cyano, amide, ester, keto, or aldehyde (preferably cyano).

Compounds of formula I preferably contain one or two Y—$P_g$ groups. More preferably, the compounds contain one Y—$P_g$ group.

Compounds of formula I may include compounds of formula I-1, which are compounds of formula I wherein m and n are independently 0 or 1, or alternatively both are 0.

Compounds of formulae I and I-1 may include compounds of formula I-2, which are compounds of formula I, or I-1 wherein m is 1 and $R^1$ is $C_1$-$C_6$ alkyl, preferably ethyl or methyl.

Compounds of formulae I, I-1, and I-2 may include compounds of formula I-3, which are compounds of formula I, I-1, or I-2 wherein n is 1 and $R^2$ is $C_1$-$C_6$ alkyl, preferably ethyl or methyl.

Compounds of formulae I, I-1, I-2, and I-3 may include compounds of formula I-4, which are compounds of formula I, I-1, I-2, or I-3 wherein R is H, or $C_1$-$C_6$ alkyl. Preferably, R in the group T is H.

Compounds of formulae I, I-1, 1-2, 1-3, and I-4 may include compounds of formula I-5, which are compounds of formula I, I-1, I-2, I-3, or I-4 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making contact lenses. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

Compounds of formulae I, I-1, 1-2, I-3, I-4, and I-5 may include compounds of formula I-6, which are compounds of formula I, I-1, I-2, I-3, I-4, or I-5 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene ($-CH_2CH_2-$). When T in the compound of formula I is O, it is preferred that the carbon atom of the linking group to which the O is attached be hindered. For instance, if T is O and Y is alkylene, a preferred alkylene is $-C(R^H)_2(CH_2)_x-$, where $R^H$ is independently $C_1$-$C_6$ alkyl (preferably independently methyl or ethyl) and x is from 1 to 5.

Compounds of formulae I, I-1, I-2, I-3, I-4, I-5, and I-6 may include compounds of formula I-7, which are compounds of formula I, I-1, I-2, I-3, I-4, I-5, or I-6 wherein T is a bond or is NR (preferably NH).

Compounds of formula I may include compounds of formula II:

Formula II

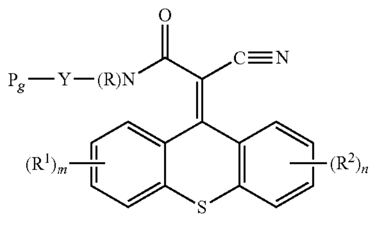

wherein:

m and n are independently 0, 1, 2, 3, or 4;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$; and $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring. Compounds of formula II preferably contain one or two Y—$P_g$ groups. More preferably, the compounds contain one Y—$P_g$ group.

Compounds of formulae II may include compounds of formula II-1, which are compounds of formula II wherein m and n are independently 0 or 1, or alternatively both are 0.

Compounds of formulae II, and II-1 may include compounds of formula II-2, which are compounds of formula II, or II-1 wherein m is 1 and $R^1$ is $C_1$-$C_6$ alkyl, preferably ethyl or methyl.

Compounds of formulae II, II-1, and II-2 may include compounds of formula II-3, which are compounds of formula II, II-1, or II-2 wherein n is 1 and $R^2$ is $C_1$-$C_6$ alkyl, preferably ethyl or methyl.

Compounds of formulae II, II-1, II-2, and II-3 may include compounds of formula II-4, which are compounds of formula II, II-1, II-2, or II-3 wherein R at each occurrence is independently H, or $C_1$-$C_6$ alkyl. Preferably, R at each occurrence is H. Preferably R in the group T is H.

Compounds of formulae II, II-1, II-2, II-3, and II-4 may include compounds of formula II-5, which are compounds of formula II, II-1, II-2, II-3, or II-4 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making polymeric devices. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

Compounds of formulae II, II-1, II-2, II-3, II-4, and II-5 may include compounds of formula II-6, which are compounds of formula II, II-1, II-2, II-3, II-4, or II-5 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene ($-CH_2CH_2-$).

Specific examples of compounds of formula I include, but are not limited to, the compounds shown in Table A.

TABLE A

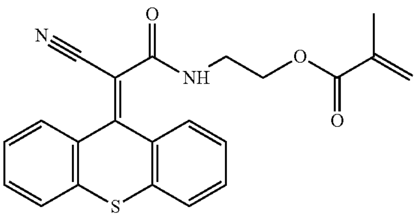

2-(2-cyano-2-(9H-thioxanthen-9-ylidene) acetamido)ethyl methacrylate

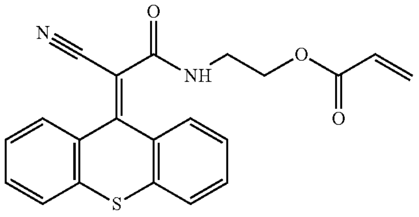

2-(2-cyano-2-(9H-thioxanthen-9-ylidene) acetamido)ethyl acrylate

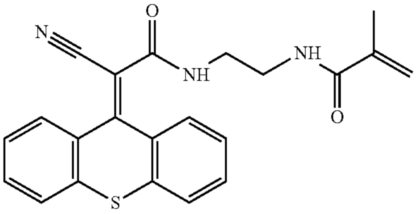

N-(2-(2-cyano-2-(9H-thioxanthen-9-ylidene) acetamido)ethyl)methacrylamide

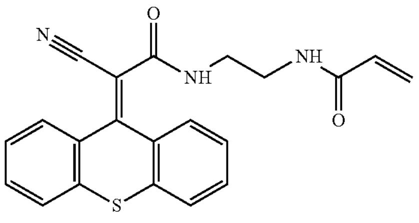

N-(2-(2-cyano-2-(9H-thioxanthen-9-ylidene) acetamido)ethyl)acrylamide

TABLE A-continued

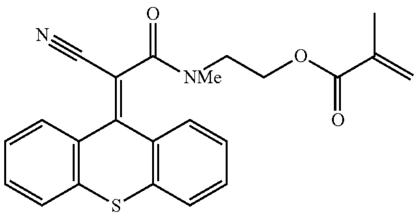

2-(2-cyano-N-methyl-2-(9H-thioxanthen-9-ylidene) acetamido)ethyl methacrylate

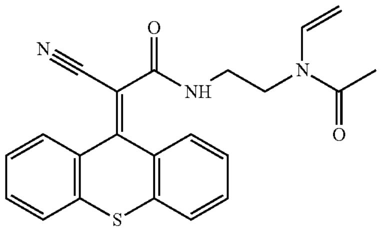

2-cyano-2-(9H-thioxanthen-9-ylidene)-N-(2-(N-vinylacetamido)ethyl)acetamide

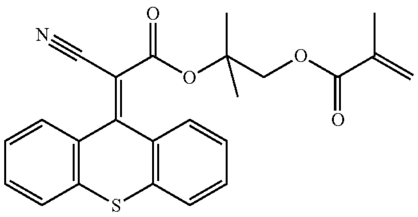

2-(2-cyano-2-(9H-thioxanthen-9-ylidene) acetamido)-2-methylpropyl methacrylate

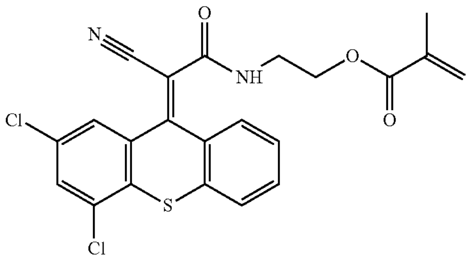

(E)-2-(2-cyano-2-(2,4-dichloro-9H-thioxanthen-9-ylidene) acetamido)ethyl methacrylate

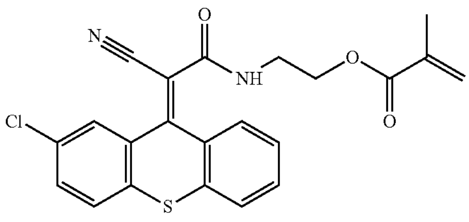

(E)-2-(2-(2-chloro-9H-thioxanthen-9-ylidene)-2-cyanoacetamido)ethyl methacrylate TABLE A-continued

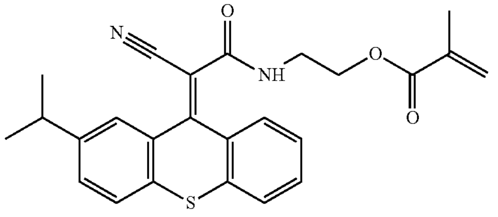

(E)-2-(2-cyano-2-(2-isopropyl-9H-thioxanthen-9-ylidene) acetamido)ethyl methacrylate

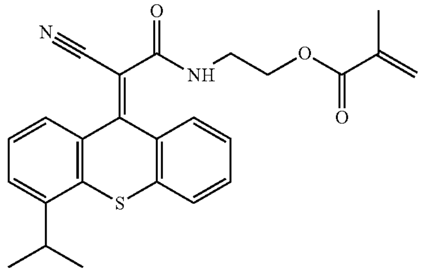

(E)-2-(2-cyano-2-(4-isopropyl-9H-thioxanthen-9-ylidene)acetamido)ethyl methacrylate

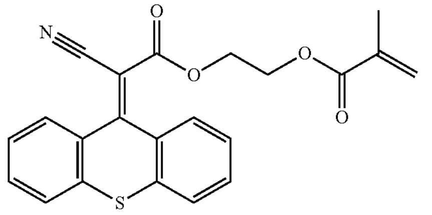

2-(2-cyano-2-(9H-thioxanthen-9-ylidene) acetoxy)ethyl methacrylate

HEV light absorbing compounds for use in the invention are preferably photostable. Thus, contact lenses of the invention, containing HEV light absorbing compounds, preferably exhibit, relative to a control lens, 20% or less, alternatively 15% or less, alternatively 10% or less, alternatively 7% or less, alternatively 5% or less, or alternatively 2% or less of change in their average transmission over a wavelength range of 380 to 450 nm, following exposure under ICH Q1B conditions.

Contact lenses of the invention may comprise other light absorbing compounds, in addition to HEV light absorbing compounds, to provide desirable absorption characteristics. For example, preferred compositions may comprise an HEV light absorbing compound and a compound that absorbs UV. Suitable UV absorbing compounds are known in the art, and fall into several classes which include, but are not limited to, benzophenones, benzotriazoles, triazines, substituted acrylonitriles, salicyclic acid derivatives, benzoic acid derivatives, cinnamic acid derivatives, chalcone derivatives, dypnone derivatives, crotonic acid derivatives, or any mixtures thereof. A preferred class of UV absorbing compound is benzotriazoles, such as Norbloc (2-(2'-hydroxy-5-methacrylyloxyethylphenyl)-2H-benzotriazole).

A particularly preferred composition comprises 2-(2-cyano-2-(9H-thioxanthen-9-ylidene)acetamido)ethyl methacrylate and a UV absorbing compound, such as a benzotriazole, for instance (2-(2'-hydroxy-5-methacrylyloxyethylphenyl)-2H-benzotriazole).

Compounds of formula I may be prepared by those skilled in the art using literature methods. By way of example, various compounds of formula I may be prepared as shown in Scheme 1 and the associated description. Exemplary reagents and procedures for these reactions appear in the working examples.

Scheme 1

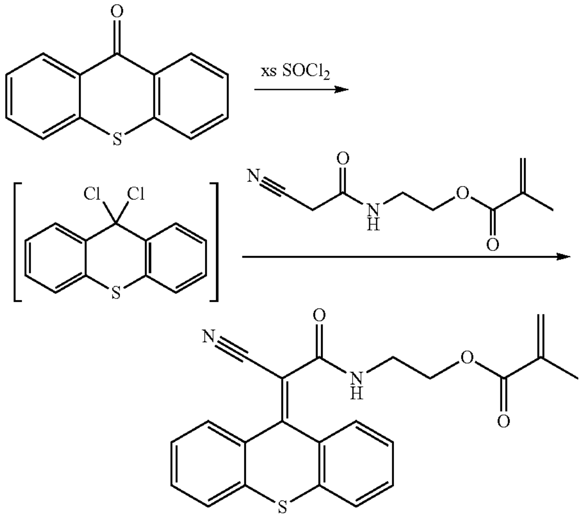

Scheme 1 shows a method for preparing exemplary compounds of the invention. Thus, the carbonyl moiety of the starting material is converted to a reactive dihalide intermediate, which is further reacted with the active methylene compound without further purification or isolation. The reaction mixture is protected from air and moisture until completion of the reaction with the cyanomethyl amide derivative. Other compounds of the invention may be prepared by those skilled in the art using analogous procedures to those shown in Scheme 1 with appropriate substitution of reagents.

High energy visible light absorbing compounds, such as the compounds of formula I, may be included in reactive mixtures to form contact lenses. Generally, the high energy visible light absorbing compounds can be present in any amount, typically up to the limit of their solubility. For instance, the compounds may be present in an amount in the range of about 0.1% to about 10% by weight, or from about 0.5 to about 5% by weight, or from about 0.75% to about 4% by weight. The upper limit is typically determined by the solubility of the compound with other co-monomers and or diluents in the reactive monomer mix.

A variety of contact lenses may be prepared, including hard contact lenses and soft contact lenses. Preferably, the contact lens is a soft contact lens, which may be made from conventional or silicone hydrogel formulations. The contact lens may be a toric contact lens, such as a toric hydrogel contact lens or a toric silicone hydrogel contact lens. Such lenses may be used to correct astigmatism in wearers needing astigmatism correction. The contact lens may also be a multifocal contact lens. Such lenses may be used to correct presbyopia in wearers needing presbyopia correction.

Contact lenses of the invention comprise a free radical reaction product of a reactive mixture containing one or more HEV light absorbing compounds, such as compounds of formula I, one or more monomers suitable for making the desired ophthalmic device (also referred to herein as device forming monomers or hydrogel forming monomers), and optional components. Thus, the reactive mixture may, for example, include, in addition to a high energy visible light absorbing compound as described above, one or more of: hydrophilic components, hydrophobic components, silicone-containing components, wetting agents such as polyamides, crosslinking agents, and further components such as diluents and initiators.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth) acrylamide, N-(3-hydroxybutyl) (meth)acrylamide, N-(4-hydroxybutyl) (meth)acrylamide, 2-aminoethyl (meth) acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth) acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

Formula A

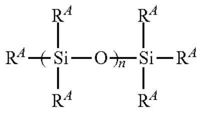

wherein:

at least one $R^A$ is a group of formula $R_g$-L- wherein $R_g$ is a polymerizable group and L is a linking group, and the remaining $R^A$ are each independently:

(a) $R_g$-L-, (b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof, (c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof, (d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof, (e) halo, (f) alkoxy, cyclic alkoxy, or aryloxy, (g) siloxy, (h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or (i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Examples of silicone-containing components suitable for use in the invention include, but are not limited to, compounds listed in Table B. Where the compounds in Table B contain polysiloxane groups, the number of SiO repeat units in such compounds, unless otherwise indicated, is preferably from 3 to 100, more preferably from 3 to 40, or still more preferably from 3 to 20.

TABLE B

| | |
|---|---|
| 1 | mono-methacryloxypropyl terminated mono-n-butyl terminated polydimethylsiloxanes (mPDMS) (preferably containing from 3 to 15 SiO repeating units) |
| 2 | mono-acryloxypropyl terminated mono-n-butyl terminated polydimethylsiloxane |
| 3 | mono(meth)acryloxypropyl terminated mono-n-methyl terminated polydimethylsiloxane |
| 4 | mono(meth)acryloxypropyl terminated mono-n-butyl terminated polydiethylsiloxane |
| 5 | mono(meth)acryloxypropyl terminated mono-n-methyl terminated polydiethylsiloxane |
| 6 | mono(meth)acrylamidoalkylpolydialkylsiloxanes |
| 7 | mono(meth)acryloxyalkyl terminated mono-alkyl polydiarylsiloxanes |
| 8 | 3-methacryloxypropyltris(trimethylsiloxy)silane (TRIS) |
| 9 | 3-methacryloxypropylbis(trimethylsiloxy)methylsilane |
| 10 | 3-methacryloxypropylpentamethyl disiloxane |
| 11 | mono(meth)acrylamidoalkylpolydialkylsiloxanes |
| 12 | mono(meth)acrylamidoalkyl polydimethylsiloxanes |
| 13 | N-(2,3-dihydroxypropane)-N'-(propyl tetra(dimethylsiloxy) dimethylbutylsilane)acrylamide |
| 14 | N-[3-tris(trimethylsiloxy)silyl]-propyl acrylamide (TRIS-Am) |
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |

TABLE B-continued
17
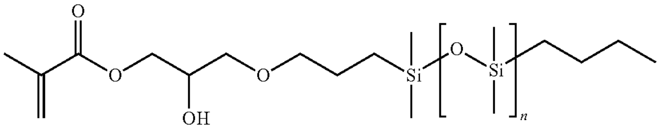
mono-(2-hydroxy-3-methacryloxypropyloxy)-propyl terminated
mono-n-butyl terminated polydimethylsiloxanes (OH-mPDMS)
(containing from 4 to 30, or from 4 to 20, or from 4 to 15 SiO repeat units)
18
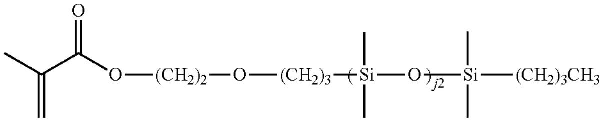
19
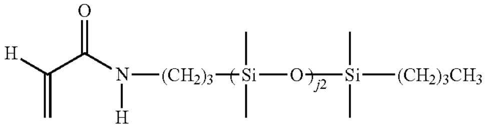
20
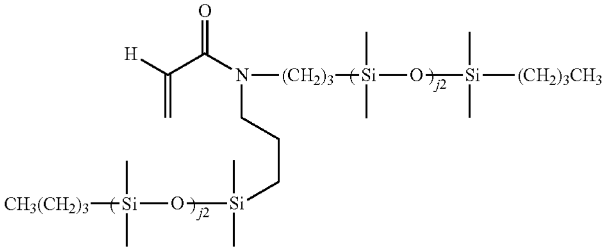
21
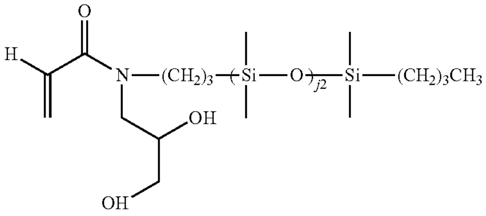
22
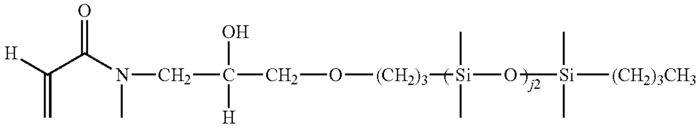
23
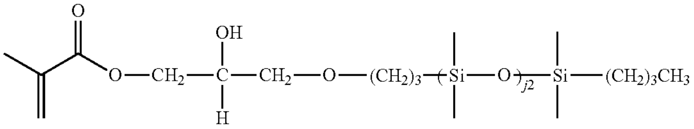
24
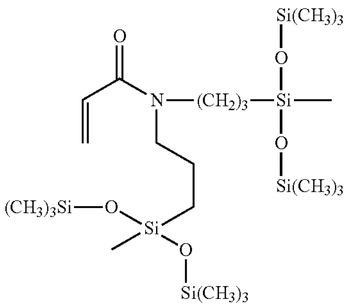

Additional non-limiting examples of suitable silicone-containing components are listed in Table C. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE C

| | |
|---|---|
| 25 | 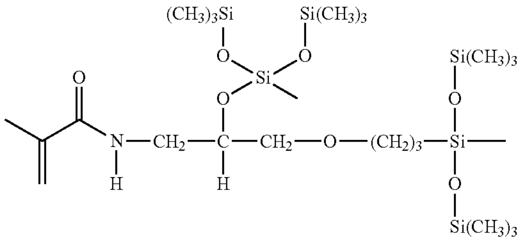 |
| 26 | 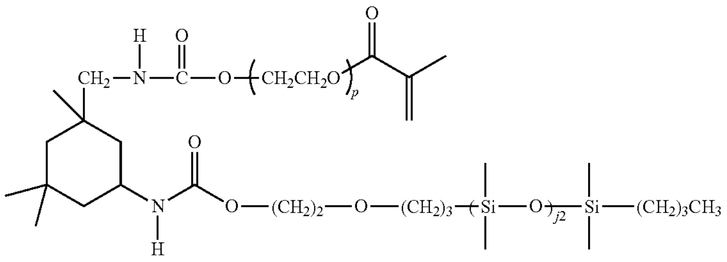<br>p is 1 to 10 |
| 27 | 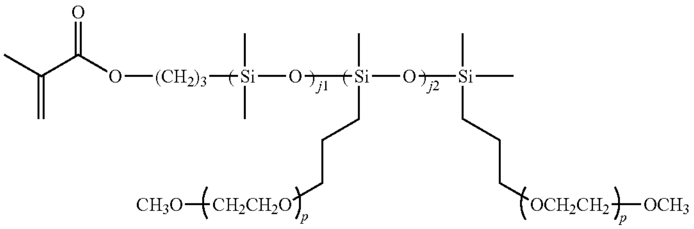<br>p is 5-10 |
| 28 | 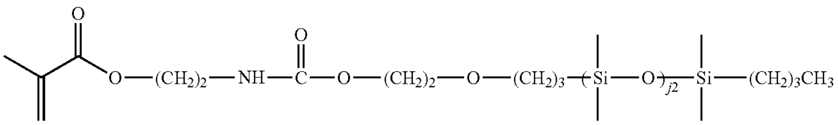 |
| 29 | 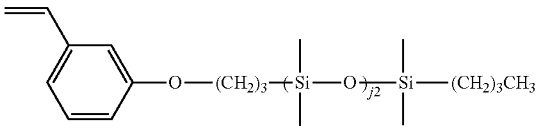 |
| 30 | 1,3-bis[4-(vinyloxycarbonyloxy)but-1-yl]tetramethyl-disiloxane |
| 31 | 3-(vinyloxycarbonylthio) propyl-[tris (trimethylsiloxy)silane] |
| 32 | 3-[tris(trimethylsiloxy)silyl] propyl allyl carbamate |
| 33 | 3-[tris(trimethylsiloxy)silyl] propyl vinyl carbamate |
| 34 | tris(trimethylsiloxy)silylstyrene (Styryl-TRIS) |

TABLE C-continued

35

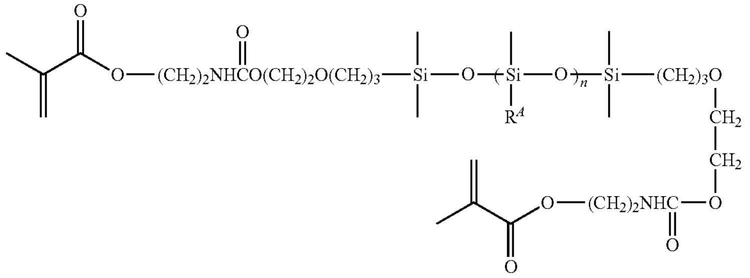

$R^A = CH_3$ (a) or $CH_2CH_2CF_3$ (b) or $CH_2-(CH_2)_2-[OCH_2CH_2]_{1-10}-OCH_3$ (c); a + b + c = n

36

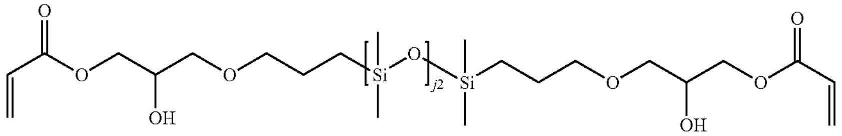

37

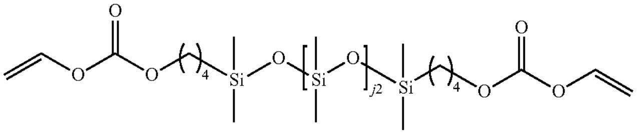

38

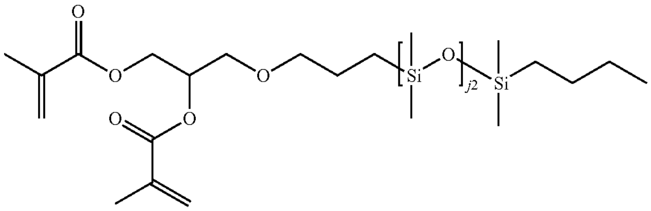

39

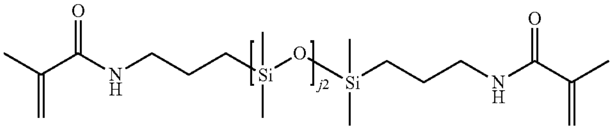

40

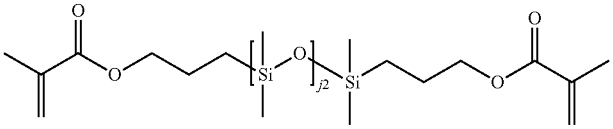

41

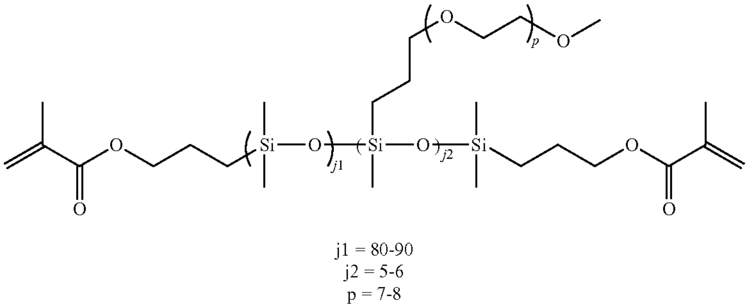

j1 = 80-90
j2 = 5-6
p = 7-8

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

Formula G1

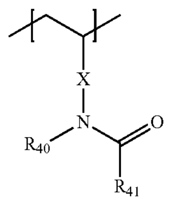

Formula G2

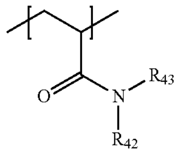

wherein X is a direct bond, —(CO)—, or —(CONHR$_{44}$)—, wherein R$_{44}$ is a $C_1$ to $C_3$ alkyl group; R$_{40}$ is selected from H, straight or branched, substituted or unsubstituted $C_1$ to $C_4$ alkyl groups; R$_{41}$ is selected from H, straight or branched, substituted or unsubstituted $C_1$ to $C_4$ alkyl groups, amino groups having up to two carbon atoms, amide groups having up to four carbon atoms, and alkoxy groups having up to two carbon groups; R$_{42}$ is selected from H, straight or branched, substituted or unsubstituted $C_1$ to $C_4$ alkyl groups; or methyl, ethoxy, hydroxyethyl, and hydroxymethyl; R$_{43}$ is selected from H, straight or branched, substituted or unsubstituted $C_1$ to $C_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted $C_1$ to $C_2$ alkyl groups. X may be a direct bond, and R$_{40}$ and R$_{41}$ may be independently selected from H, substituted or unsubstituted $C_1$ to $C_2$ alkyl groups. R$_{42}$ and R$_{43}$ can be independently selected from H, substituted or unsubstituted $C_1$ to $C_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N, N'-dimethylurea, N, N-dimethylacrylamide, methacrylamide, and acyclic amides of Formulae G2 and G3:

Formula G2

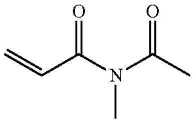

Formula G3

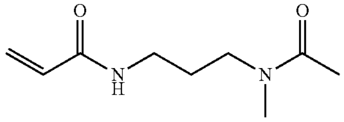

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

Formula G4

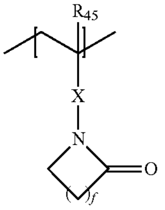

wherein R$_{45}$ is a hydrogen atom or methyl group; wherein f is a number from 1 to 10; wherein X is a direct bond, —(CO)—, or —(CONHR$_{46}$)—, wherein R$_{46}$ is a $C_1$ to $C_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9,2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Reactive mixtures of the invention preferably include up to eleven weight percent of a polyamide internal wetting agent, alternatively less than 11 weight percent, alternatively 9 weight percent or less, alternatively less than 9 weight percent, alternatively 8 weight percent or less, or alternatively 7 weight percent or less, of a polyamide internal wetting agent. Preferably, the polyamide internal wetting agent is a high molecular weight (weight average molecular weight of at least 100,000 daltons) polyvinylpyrrolidone (PVP) homopolymer.

Cross-Linking Agents

It is generally desirable to add one or more cross-linking agents, also referred to as cross-linking monomers, multi-functional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes α,ω-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as compounds of Formula E (and its sub-formulae) and the multi-functional compounds shown in Table C.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine oxide (Irgacure 819), 2,4,6-trimethylbenzyldiphenyl phosphine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B.V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the contact lenses of the invention may comprise, in addition to a high energy visible light absorbing compound, any of the polymerizable compounds and optional components described above.

Preferred reactive mixtures may comprise: a high energy visible light absorbing compound, such as a formula I compound, and a hydrophilic component.

Preferred reactive mixtures may comprise: a high energy visible light absorbing compound, such as a formula I compound, and a hydrophilic component selected from DMA, NVP, HEMA, VMA, NVA, methacrylic acid, and mixtures thereof. Preferred are mixtures of HEMA and methacrylic acid.

Preferred reactive mixtures may comprise: a high energy visible light absorbing compound, such as a formula I compound, a hydrophilic component, and a silicone-containing component.

Preferred reactive mixtures may comprise: a high energy visible light absorbing compound, such as a formula I compound, a hydrophilic component, and a silicone-containing component comprising a compound of formula A.

Preferred reactive mixtures may comprise: a high energy visible light absorbing compound, such as a formula I compound, a hydrophilic component selected from DMA, NVP, HEMA, VMA, NVA, and mixtures thereof, a silicone-containing component such as a compound of formula A; and an internal wetting agent.

Preferred reactive mixtures may comprise: a high energy visible light absorbing compound, such as a formula I compound, a hydrophilic component selected from DMA, HEMA and mixtures thereof, a silicone-containing component selected from 2-hydroxy-3-[3-methyl-3,3-di(trimethylsiloxy)silylpropoxy]-propyl methacrylate (SiMAA), monomethacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof, and a wetting agent (preferably PVP or PVMA). For the hydrophilic component, mixtures of DMA and HEMA are preferred. For the silicone containing component, mixtures of SiMAA and mPDMS are preferred.

Preferred reactive mixtures may comprise: a high energy visible light absorbing compound, such as a formula I compound, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

Preferred reactive mixtures may comprise: a high energy visible light absorbing compound, such as a formula I compound; between about 1 and about 15 wt % of at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g., OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first mono-functional, hydroxyl substituted poly(disubstituted siloxane) and the second hydroxyl substituted poly(disubstituted siloxane) are present in concentrations to provide a ratio of weight percent of the first mono-functional, hydroxyl substituted poly(disubstituted siloxane) to weight percent of the second hydroxyl substituted poly(disubstituted siloxane) of 0.4-1.3, or 0.4-1.0.

The foregoing reactive mixtures may contain optional ingredients such as, but not limited to, one or more initiators, internal wetting agents, crosslinkers, other UV or HEV absorbers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic devices are contact lenses, more preferably soft hydrogel contact lenses. The transmission wavelengths and percentages described herein may be measured on various thicknesses of lenses using, for instance, the methodologies described in the Examples. By way of example, a preferred center thickness for measuring transmission spectra in a soft contact lens may be from 80 to 100 microns, or from 90 to 100 microns or from 90 to 95 microns. Typically, the measurement may be made at the center of the lens using, for instance, a 4 nm instrument slit width. Various concentrations of the one or more high energy visible light absorbing compounds may be used to achieve the transmission characteristics described above. For instance, the concentration may be in the range of at least 1 percent, or at least 2 percent; and up to 10 percent, or up to 5 percent, based on the weight percentages of all components in the reactive mixture, excluding diluent. A typical concentration may be in the range of 3 to 5 percent.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

- Water concentration %: at least 20%, or at least 25% and up to 80% or up to 70%
- Haze: 30% or less, or 10% or less
- Advancing dynamic contact angle (Wilhelmy plate method): 1000 or less, or 800 or less; or 500 or less
- Tensile Modulus (psi): 150 or less, or 135 or less, 120 or less, or 80 to 135
- Oxygen permeability (Dk, barrers): at least 60 barrers, or at least 80, or at least 100, or at least 150, or at least 200
- Elongation to Break: at least 100

For ionic silicon hydrogels, the following properties may also be preferred (in addition to those recited above):

- Lysozyme uptake (μg/lens): at least 100, or at least 150, or at least 500, or at least 700
- Polyquaternium 1 (PQ1) uptake (%): 15 or less, or 10 or less, or 5 or less.

Contact lenses of the invention may be used to improve one or more vision attributes in a contact lens wearer. The vision attribute may be photostress recovery time. The vision attribute may be glare discomfort. The vision attribute may be glare disability threshold. The vision attribute may be heterochromatic contrast threshold. The vision attribute may be halo size. The vision attribute may be starburst size. The vision attribute may be light scattering. The vision attribute may be one or more of photostress recovery time, glare discomfort, glare disability threshold, heterochromatic contrast threshold, halo size, starburst size, and light scattering. Further details regarding improvements in visual attributes are provided in the Examples below.

EXAMPLES

UV/Vis Spectra

Ultraviolet-visible spectra of compounds in solution were measured on a Perkin Elmer Lambda 45 or an Agilent Cary 6000i UV/VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected. For the Cary instrument, the scan range was 200-800 nm; the scan speed was 600 nm/min; the slit width was 2 nm; the mode was transmission or absorbance; and baseline correction was selected. A baseline correction was performed before samples were analyzed using the autozero function.

Ultraviolet-visible spectra of contact lenses formed in part from the claimed compositions were measured on a Perkin Elmer Lambda 45 UV/VIS or an Agilent Cary 6000i UV/VIS scanning spectrometer using packing solution. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission; and baseline correction was selected. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

The following abbreviations will be used throughout the Examples and Figures and have the following meanings:

- BC: back or base curve plastic mold
- FC: front curve plastic mold
- DMA: N, N-dimethylacrylamide (Jarchem)
- HEMA: 2-hydroxyethyl methacrylate (Bimax)
- PVP: poly(N-vinylpyrrolidone) (ISP Ashland)
- PDMA: polydimethylacrylamide
- PVMA: polyvinylmethyacetamide
- EGDMA: ethylene glycol dimethacrylate (Esstech)
- TEGDMA: tetraethylene glycol dimethacrylate (Esstech)
- Irgacure 819: bis(2,4,6-trimethylbenzoyl)-phenylphosphineoxide (BASF or Ciba Specialty Chemicals)
- Irgacure 1870: blend of bis(2,6-dimethoxybenzoyl)-2,4,4-trimethyl-pentylphosphineoxide and 1-hydroxy-cyclohexyl-phenyl-ketone (BASF or Ciba Specialty Chemicals)

mPDMS: mono-n-butyl terminated monomethacryloxypropyl terminated polydimethylsiloxane ($M_n$=800-1000 daltons) (Gelest)

HO-mPDMS: mono-n-butyl terminated mono-(2-hydroxy-3-methacryloxypropyloxy)-propyl terminated polydimethylsiloxane ($M_n$=400-1500 daltons) (Ortec or DSM-Polymer Technology Group)

ac-PDMS: bis-3-acryloxy-2-hydroxypropyloxypropyl polydimethylsiloxane (Tegomer V-Si 2250 from Evonik)

Blue HEMA: 1-amino-4-[3-(4-(2-methacryloyloxy-ethoxy)-6-chlorotriazin-2-ylamino)-4-sulfophenylamino]anthraquinone-2-sulfonic acid, as described in U.S. Pat. No. 5,944,853 Da: dalton or g/mole kDa: kilodalton or an atomic mass unit equal to 1,000 daltons SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5-heptamethyltrisiloxan-3-yl)propoxy)-2-hydroxypropyl methacrylate RB247: 1,4-Bis[2-methacryloxyethylamino]-9,10-anthraquinone BHT: butylated hydroxytoluene D3O: 3,7-dimethyl-3-octanol (Vigon)

DIW: deionized water

MeOH: methanol

IPA: isopropyl alcohol

HCl: hydrochloric acid $CH_2Cl_2$ or DCM: methylene chloride or dichloromethane $SOCl_2$: thionyl chloride mCPBA: m-chloroperbenzoic acid EtOAc: ethyl acetate $NH_2CH_2CH_2OH$: ethanolamine or 2-aminoethanol Norbloc: 2-(2'-hydroxy-5-methacrylyloxyethylphenyl)-2H-benzotriazole (Janssen)

PP: polypropylene which is the homopolymer of propylene

TT: Tuftec which is a hydrogenated styrene butadiene block copolymer (Asahi Kasei Chemicals)

Z: Zeonor which is a polycycloolefin thermoplastic polymer (Nippon Zeon Co Ltd)

TL03 lights: Phillips TLK 40 W/03 bulbs

LED: light emitting diode $^1$N NMR: proton nuclear magnetic resonance spectroscopy UV-VIS: ultraviolet-visible spectroscopy L: liter mL: milliliter Equiv. or eq.: equivalent kg: kilogram g: gram mol: mole mmol: millimole min: minute(s)

nm: nanometer(s)

TLC: thin layer chromatography

Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.

Example 1—Synthesis of 2-(2-cyanoacetamido) ethyl methacrylate (A) and 2-(2-cyano-2-(9H-thioxanthen-9-ylidene)acetamido)ethyl methacrylate (B) as Shown in Scheme 2

Scheme 2

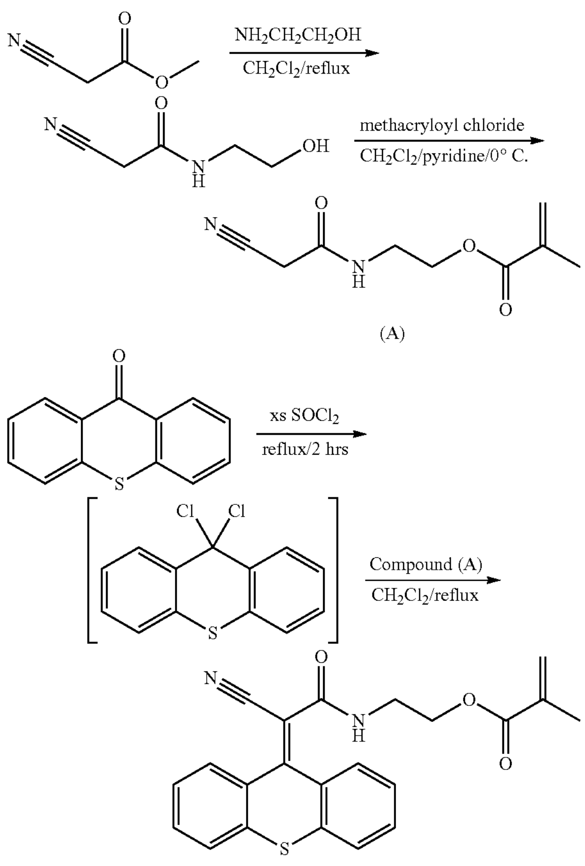

(A)

(B)

Methyl cyanoacetate (40 grams, 0.4037 mole) and 25 mL of dichloromethane were stirred in a 3 neck, 500 mL round bottom flask under equipped with a reflux condenser under a nitrogen environment. 2-aminoethanol (23.8 grams, 0.3897 mole, ~0.97 eq.) was added to the solution via an addition funnel, after which the temperature rose and the methylene chloride began to reflux. After the exotherm ceased, external heat was applied to continue a gentle reflux for a total of two hours, after which no ethanolamine was observed by thin layer chromatography.

The reaction may also be conducted at room temperature and is complete within a few hours.

The mixture was cooled to room temperature and all the methylene chloride was evaporated at reduced pressure. The residual oil was washed three times with 50 mL of ethyl acetate to remove unreacted starting material and non-polar impurities. The residual ethyl acetate was then removed under reduced pressure, and the resulting oil was used for acylation without any further purification.

The crude N-2-hydroxyethylacetamide derivative was dissolved in 150 mL of dichloromethane containing 40 grams of pyridine (~0.5 mole) in a three-neck round bottom flask equipped with a reflux condenser, an addition funnel, and a magnetic stirring bar. The flask was immersed in an ice bath and allowed to cool down to around 0° C. Methacryloyl chloride (45.76 grams, ~0.44 mole) was added dropwise from the addition funnel, and the resulting reaction mixture was allowed to warm up to room temperature while constantly stirring the system. Methanol (20 mL) was the added to the flask to quench any unreacted methacryloyl chloride. The volatile components were removed by rotary evaporation under reduced pressure, and the crude product dissolved in 800 mL of dilute aqueous HCl. The resulting aqueous solution was extracted three times with 100 mL of hexanes in a separatory funnel to remove any non-polar impurities. The organic layers were discarded. Sodium chloride was added to the aqueous layer which was then extracted three times with 300 mL of ethyl acetate. About 50 milligrams of BHT were added to the combined organic fractions as an inhibitor, and the ethyl acetate removed by rotary evaporation under reduced pressure. The crude product crystalized out of solution during solvent removal. When about 100 mL of ethyl acetate was left in the flask, 250 mL of hexanes was added, and the crude product was isolated by vacuum filtration using a fritted glass funnel. Thin layer chromatography indicated the presence of a single compound. The filter cake was washed two times with 150 mL of hexanes and then vacuum dried at 40° C., yielding 53 grams (about 70% yield) of 2-(2-cyanoacetamido)ethyl methacrylate (A). $^1$H NMR (500 MHz, $CDCl_3$) δ 1.93 (3H, s, $CH_3$), 3.36 (2H, s, $CNCH_2$), 3.60 (2H, dd, $CH_2NH$), 4.26 (2H, t, $CH_2OC{=}O$), 5.59 (1H, m, vinylic), 6.11 (1H, bs, vinylic), 6.52 (1H, bs, NH).

A mixture of 9H-thioxanthene-9-one (2.12 grams, 0.01 mole) and thionyl chloride (5 mL, 8.2 grams, ~0.07 mole) was refluxed in a 50 mL round bottom flask under a nitrogen atmosphere with constant stirring. After two hours, the red solution was evaporated to dryness ensuring that all unreacted thionyl chloride was removed from the system. 2-(2-Cyanoacetamido)ethyl methacrylate (A) (2.3 grams, 0.0117 mole, ~1.17 eq.) and 15 mL of dichloromethane were added, and the resulting reaction mixture was heated to reflux under a nitrogen blanket. The reaction was monitored by thin layer chromatography. After two hours, no changes were observed in the chromatogram, so the reactive mixture was allowed to cool down to room temperature. 2-(2-cyano-2-(9H-thioxanthen-9-ylidene)acetamido)ethyl methacrylate (B) was isolated as yellow crystals (3.2 grams, 82% yield) after passing through a short silica gel column ($CH_2Cl_2$, followed by 8 weight % EtOAc in $CH_2Cl_2$). The UV-VIS transmission spectrum of a 0.2 mM methanol solution Compound B is shown in FIG. 1. $^1$H NMR (500 MHz, $CDCl_3$) δ 1.84 (3H, s, $CH_3$), 3.47 (2H, m, $CH_2NH$), 4.01 (2H, t, $CH_2OC{=}O$), 5.55 (1H, m, vinylic), 5.91 (1H, bs, NH), 5.98 (1H, bs, vinylic), 7.24 (1H, t, Ar—H), 7.31 (1H, t, Ar—H), 7.39 (2H, m, Ar—H), 7.49 (1H, d, Ar—H), 7.55 (1H, m, Ar—H), 7.61 (1H, d, Ar—H), 8.04 (1H, m, Ar—H).

Example 2—Synthesis of 2-(2-cyanoacetamido) ethyl methacrylate (F) and N-(2-(2-cyano-2-(9H-thioxanthen-9-ylidene)acetamido)ethyl)methacrylamide (G) as Shown in Scheme 3

Scheme 3

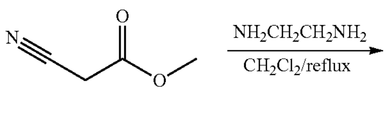

-continued

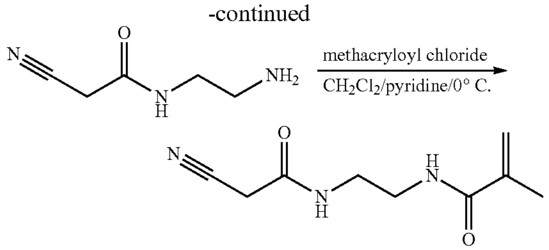

(F)

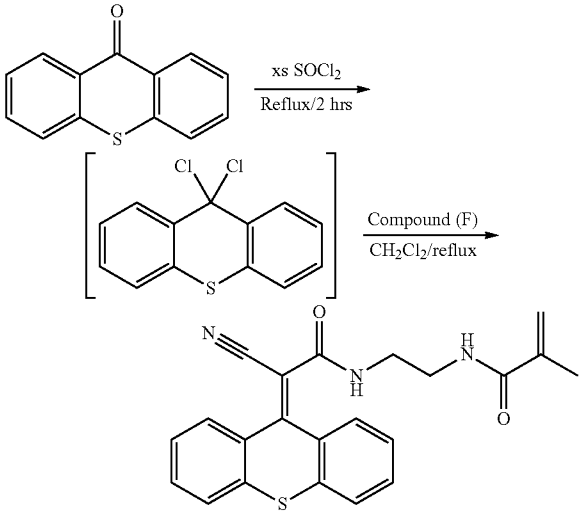

(G)

Methyl cyanoacetate (22 grams, 0.22 mole) and 250 mL of dichloromethane were stirred in a 3 neck, 500 mL round bottom flask under equipped with a reflux condenser under a nitrogen environment. The solution is cooled in a water bath and 1,2-diaminoethane (12 grams, 0.2 mole, ~0.9 eq.) added to the mixture. As the reaction progresses, the mixture appears more and more heterogenous, with the product crashing out of solution. After four hours of stirring at room temperature, the volatiles are evaporated under reduced pressure and the residue is washed with ethyl acetate over a fritted glass funnel and dried at 50° C. prior to further use. $^1$H NMR (500 MHz, $D_2O$) δ 2.74 (2H, t, $CH_2NH_2$), 3.29 (2H, t, $CH_2NH$), 3.38 (2H, s, $CH_2CN$).

2-aminoethyl cyanoacetamide (12.7 g, 0.1 mole) and 12.0 grams of sodium carbonate are stirred in 150 mL of methanol while being chilled in an ice bath. Methacryloyl chloride (11.5 g, 1.1 eq.) is added to the suspension in a dropwise manner, while maintaining the reaction temperature below 30° C. at all times. Once the reaction is complete, evaporate all volatiles under reduced pressure, redissolve the product in acetonitrile and filter the solution to remove all the salts present. Evaporate the acetonitrile under reduced pressure and wash the resulting solids with ethyl acetate over a fritted glass funnel to obtain the desired 2-(2-cyanoacetamido)ethyl methacrylamide (F). $^1$H NMR (500 MHz, $CD_3OD$) δ 1.86 (3H, s, $CH_3$), 3.22-3.26 (4H, m, NH, $CH_2CN$), 3.29 (4H, m, $CH_2NH$), 5.31 (1H, m, vinylic), 5.63 (1H, m, vinylic).

A mixture of thioxanthone (4.24 grams, 0.02 mole) and 8 mL of thionyl chloride (13.12 grams, ~0.11 mole) was gently refluxed under a nitrogen atmosphere with constant stirring. After two hours of heating, the solution was evaporated to dryness under reduced pressure, ensuring that all unreacted thionyl chloride was removed. 2-(2-cyanoacetamido)ethyl methacrylamide (F) (4.2 grams, ~1.1 eq.) and 20 mL of degassed methylene chloride were added to the flask, and the mixture was gently refluxed for 3 hours under a nitrogen environment, while monitoring the progress by TLC. The volatiles were evaporated under reduced pressure, and the organics are washed with ethyl acetate. Large quantities of a precipitate enriched with the major product were observed. The suspension was filtered, and the residual solids washed with ethyl acetate prior to drying in a vacuum oven. The UV-VIS transmission spectrum of a 0.2 mM methanolic solution of Compound G is shown in FIG. 2. $^1$H NMR (500 MHz, $CDCl_3$) δ 1.89 (3H, s, $CH_3$), 3.26 (2H, m, $CH_2NH$), 3.32 (2H, m, $CH_2NH$), 5.33 (1H, m, vinylic), 5.68 (1H, m, vinylic), 6.63 (1H, m, NH), 6.49 (1H, m, NH), 7.25 (1H, m, Ar—H), 7.33 (1H, dt, Ar—H), 7.39 (2H, m, Ar—H), 7.51-7.59 (3H, m, Ar—H), 8.05 (1H, m, Ar—H).

Example 3—Synthesis of 2-(2-cyanoacetoxy)ethyl methacrylate (K) and 2-(2-cyano-2-(9H-thioxanthen-9-ylidene)acetoxy)ethyl methacrylate (L) as Shown in Scheme 4

Scheme 4

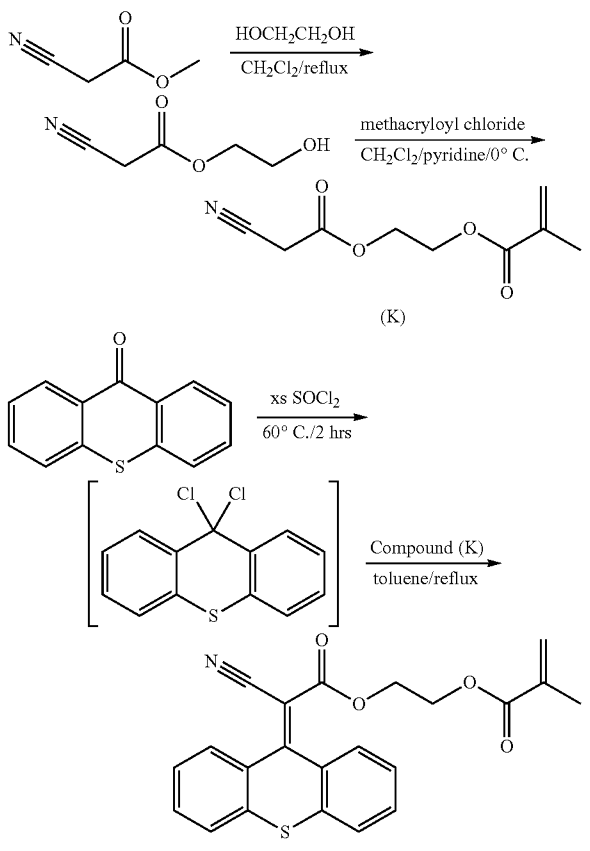

(K)

(L)

2-(2-Cyanoacetoxy)ethyl methacrylate (K) was prepared by coupling cyanoacetic acid with 2-hydroxyethyl methacrylate as follows. Cyanoacetic acid (9 g, 0.106 mole) and 13 g of 2-hydroxyethyl methacrylate (HEMA, are stirred in 250 mL of dichloromethane, and ethyl dimethylaminopropyl carbodiimide hydrochloride (EDC) is added to the suspension in 4 batches of 5 grams each (20 g, 0.104 mole). The mixture gradually becomes more homogenous as the less polar derivative is formed and volatiles are evaporated under reduced pressure after completion of the reaction. The product is redissolved in a 25:75 mixture of ethyl acetate and hexanes by weight and extracted several times with deionized water to remove any residual salts and unreacted HEMA. A small amount of 4-methoxyhydroquinone (<20 mg) is added to the organic layer and the product is obtained pure after evaporation of the solvents under reduced pressure. $^1$H NMR (500 MHz, $CDCl_3$) δ 1.92 (3H, m, $CH_3$), 3.47 (2H, S, $NCCH_2$), 4.36 (2H, m, $OCH_2$), 4.44 (2H, m, $OCH_2$), 4.59 (1H, m, vinylic), 6.10 (1H, m, vinylic).

A mixture of thioxanthone (4.24 grams, 0.02 mole) and 8 mL of thionyl chloride (13.12 grams, ~0.11 mole) was gently refluxed under a nitrogen atmosphere with constant stirring. After two hours of heating, the solution was evaporated to dryness under reduced pressure, ensuring that all unreacted thionyl chloride was removed. A solution of 2-(2-cyanoacetoxy)ethyl methacrylate (K) (4.33 grams, ~1.1 eq.) in 20 mL of degassed methylene chloride was added to the flask, and the mixture was gently refluxed for 3 hours under a nitrogen environment, while monitoring the progress by TLC. The residue was washed with methanol to remove most of the unreacted starting thioxanthone, re-concentrated, and the crude product was purified by chromatography over a silica gel plug and vacuum dried overnight. The UV-VIS transmission spectrum of a 0.2 mM solution of Compound L in dichloromethane is shown in FIG. 2. $^1$H NMR (500 MHz, $CDCl_3$) δ 1.92 (3H, s, $CH_3$), 4.36 (2H, m, $CH_2$), 4.44 (2H, m, $CH_2$), 5.59 (1H, m, vinylic), 6.10 (1H, m, vinylic), 7.24-7.62 (7H, m, Ar—H), 8.1 (1H, m, Ar—H).

Example 4—Silicone Hydrogel Formulations Comprising Compound (B)

Reactive monomer mixtures were prepared composed of 77 weight percent of the formulations listed in Table 4, and 23 weight percent of the diluent D3O. The reactive monomer mixtures were individually filtered through a 3 μm filter using a stainless-steel syringe under pressure.

TABLE 4

| Component | Ex 4A (weight %) | Ex 4B (weight %) | Ex 4C (weight %) | Ex 4D (weight %) |
|---|---|---|---|---|
| mPDMS 1000 | 30.85 | 30.7 | 30.55 | 30.39 |
| SiMAA | 27.61 | 27.48 | 27.35 | 27.2 |
| DMA | 23.76 | 23.6 | 23.53 | 23.4 |
| HEMA | 5.94 | 5.91 | 5.88 | 5.85 |
| TEGDMA | 1.52 | 1.52 | 1.51 | 1.5 |
| PVP K90 | 6.9 | 6.9 | 6.8 | 6.8 |
| Irgacure 1870 | 0.35 | 0.34 | 0.34 | 0.34 |
| RB247 | 0.02 | 0.02 | 0.02 | 0.02 |
| Compound (B) | 3.05 | 3.03 | 3.02 | 3 |
| Norbloc ® | 0 | 0.5 | 1 | 1.5 |
| Σ Components | 100 | 100 | 100 | 100 |

Formulations 4A-4D were degassed at ambient temperature by applying vacuum (40 torr) for 45 minutes. Then, in a glove box with a nitrogen gas atmosphere and less than about 0.1-0.2 percent oxygen gas, about 75 μL of the reactive mixture were dosed using an Eppendorf pipet at room temperature into the FC made of 90:10 (w/w) Zeonor/TT blend. The BC made of 90:10 (w/w) Z:TT blend was then placed onto the FC. The molds were equilibrated for a minimum of twelve hours in the glove box prior to dosing. Pallets containing eight mold assemblies each were transferred into an adjacent glove box maintained at 65° C., and the lenses were cured from the top and the bottom for 15 minutes using 435 nm LED lights having an intensity of about 2 $mW/cm^2$ at the tray's location.

The lenses were manually de-molded with most lenses adhering to the FC and released by suspending the lenses in about one liter of 70 percent IPA for about one hour, followed by soaking two more times with fresh 70 percent IPA for 30 minutes; then two times with fresh DIW for 15 minutes; then two time with packing solution for 30 minutes. The lenses were equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels. The average center thickness of each lens set was measured; 4A=87.7 microns, 4B=85.3 microns, 4C=87.3 microns, and 4D=85.7 microns.

FIGS. 1-3 show the UV-VIS spectra of the lenses made from Formulations 4A-4D demonstrating that compound (B) or combinations of compound (B) and Norbloc® may provide complete or nearly complete absorption between 300 nm and 400 nm with some absorption in the high energy visible region between 400 nm and 450 nm.

Example 5—Photostability

Silicone hydrogel contact lenses made from a reactive mixture containing compound (B) were subjected to photostability testing as described above. The spectral transmittance results at 380 to 450 nm of the lens containing compound (B) that had been photo-exposed under ICH-Q1B conditions, versus a contact lens containing compound (B) but without photo-exposure are shown Table 5. The data demonstrates that lenses containing HEV light absorbing compounds as described herein are photostable.

TABLE 5

| Power | Lens exposure | Packaging | % T (380-450 nm) | % Change |
|---|---|---|---|---|
| −3.00D | Control | Clear Blister | 37 | 5.4 |
| | ICH-QIB | Clear Blister | 39 | |
| −1.00D | Control | Clear Blister | 39 | 0 |
| | ICH-QIB | Clear Blister | 39 | |
| −6.00D | Control | Clear Blister | 38 | 0 |
| | ICH-QIB | Clear Blister | 38 | |

Example 6—VBUT Objective Clinical Study

This was a single-site, 5-visit, bilateral, 2×2 crossover, dispensing, randomized, controlled and subject-masked study. The objectives of the study were to evaluate the clinical performance of the Test lens (a lens of the invention obtained from a reactive mixture that includes mPDMS 1000, SiMAA, DMA, HEMA, Norbloc, PVP K90 (7 weight percent) and an HEV light filtering compound (Compound (B), 3 weight percent) compared to the Control Lens (a silicone hydrogel contact lens obtained from a reactive mixture that includes about 7 weight percent PVP K90, but no HEV light filter). The Test Lens transmits from 0 percent to 70 percent of light having a wavelength range of 400 to 409 nm, whereas the Control Lens transmits at least 90 percent of light across the wavelength range of 400 to 409 nm. The Control Lens is substantially identical to the Test lens, except that it does not contain Compound B.

At Visit 1, subjects were randomly assigned to one of two lens wear arms (Control/Test or Test/Control). Visit 2 and 3 evaluated the vision endpoints and physiology of Lens A. Visits 4 and 5 repeated the procedures with the alternate lens.

Subject Population and Disposition. Healthy male and female subjects between 18 through 39 years (inclusive) of age, who were habitual wearers of spherical silicone hydrogel contact lenses were included in this study. Subjects were required to have spherical equivalent of the vertex-corrected distance refraction between −1.00 and −6.00 DS (inclusive) with magnitude of the cylindrical component of the subject's vertex corrected distance refraction between 0.00 and 1.00 DC (inclusive) and best corrected, monocular, distance visual acuity to be 20/25 or better, in each eye In total, 50 subjects were enrolled from a single clinical site in this study. Of those enrolled, 47 (94.0%) subjects were randomly assigned to one of the two possible lens wear sequences (Test/Control or Control/Test), dispensed at least one study lens, and were included in the safety population, while 3 (6.0%) subjects were enrolled but not dispensed a study lens; 42 (84.0%) subjects completed the study while 5 (10.0%) subjects were discontinued. Total 41 (82.0%) subjects completed the study without any major protocol deviation and were included in the Per-Protocol Population (Table 6).

TABLE 6

Study Population Summary—All Enrolled Subjects

| Total Enrolled | Test\Control 24 | Control\Test 23 | Not Treated 3 | Total 50 |
|---|---|---|---|---|
| Per-Protocol Population n (%) | 21 (87.5) | 20 (87.0) | 0 (0.0) | 41 (82.0) |
| Safety Population n (%) | 24 (100) | 23 (100) | 0 (0.0) | 47 (94.0) |
| Intent-to-Treat Population n (%) | 24 (100) | 23 (100) | 0 (0.0) | 47 (94.0) |
| Enrolled not Dispensed n (%) | 0 | 0 | 3 (100) | 3 (6.0) |

Per-Protocol Population: All subjects who completed the study without a major protocol deviation. Safety Population: All subjects who were administered any test article excluding subjects who drop out prior to administering any test article. Intent-to-Treat Population: All randomized subjects regardless of actual treatment and subsequent withdrawal from study or deviation from protocol. Enrolled not Dispensed: Subjects who have signed the informed consent form but not administered any study articles.

Instrumentation. Optical quality metrics of the subject's eye and tear film dynamic changes can be assessed using a double pass (DP) aberrometer system and its tear film analysis software. In this study, the instrument used is the HD Analyzer™ (Visiometrics S.L., Terrassa, Spain), model OQAS-HD. A laser diode of 780 nm wavelength is emitted on the retina and DP through the ocular media, after which the light reflection is recorded by a charge-coupled camera device. The reflected light passed through the diameter of the exit pupil, which was settled at 4 mm. Pupil alignment was controlled with an additional camera, personal computer was used to process the retinal images and to collect the data. The DP images were acquired at best focus, corrected internally by an optometer that ranges from −8.00 to +6.00 diopters (D). Acquisition of images for the purpose of this study was restricted to eyes with a maximum of −0.50D residual cylinder. This instrument considers internal scattering, aberrations of the eye, and tear film effects.

Ocular Scattering Index (OSI) is an objective parameter proportional to intraocular scattering. It is calculated from the assessment of the amount of light that is on the outside of the patient's double-pass image, relative to the amount of light in its central part. Accordingly, the higher the OSI value, the greater the level of intraocular scattering. Vision Break-up Time (VBUT) is calculated using the Tear film analysis program included in the HD analyzer tear film analysis program which records dynamic changes in OSI values. The program consists of a 20 second examination with OSI measurements every 0.5 seconds (see Tan, et al., Dynamic change of optical quality in patients with dry eye disease. *Invest Ophthalmol Vis Sci.* 2015; 56(5):2848-2854). VBUT is The time elapsed in seconds from 0 seconds to the time at which the subject's vision quality index has dropped below a defined threshold. OSI is dynamically measured 40 times in a 20 second period as a surrogate of tear film stability (dOSI).

Statistical Analyses. Statistical analyses were performed using the Statistical Analysis System (SAS) software Version 9.4 (SAS Institute, Cary, NC). The vison break-up time (VBUT) was obtained by the HD analyzer instrument at 1-week follow-up. The analysis was conducted on the Intent-to-Treat (ITT) population. Given that the HD Analyzer outputted the value ">10" after 10 seconds had been reached, the VBUT scores were converted into a binary variable (0=VBUT less than or equal 10 seconds and 1=VBUT greater than 10 seconds) for the analysis purpose. The dichotomized VBUT scores were analyzed using a generalized linear mixed model with a binary distribution and logit as a link function and the probability of "1" (VBUT greater than 10 seconds) was modeled. The final model included lens type, lens sequence, period, repeated measurements, age and gender as fixed effects, and subject as a random effect (G-side). The random intercept for eyes (nested within subject) was not included in the final model because there was not enough variation in the response to attribute any variation to this random effect, controlling for everything else in the model. An unstructured (UN) covariance matrix was used to model the residual errors among repeated measurements from the same study period within the same subject and eye (R-side). The Kenward and Roger method was used for the calculation of denominator degree of freedom. Superiority was claimed if the lower bound of the 2-sided 95% CI constructed for the odds ratio (Test vs. Control) was above 1.0.

Results. Table 7 displays the estimated proportions, odds ratio and the associated 95% confidence intervals for the analysis of Vision Break-up Time (VBUT). As shown in Table 7, the Test lens demonstrated superiority compared to the Control, since the lower limit of the 95% CI for the odds ratio estimate was above 1.0. Results indicated that subjects wearing the Test lens are about 1.6 times more likely to have VBUT longer than 10 seconds compared to subjects wearing the Control lens.

TABLE 7

Exploratory Analysis of Vision Break-up Time (VBUT)—t Intent-to-Trea Population at 1-Week Follow-up Proportion and Odds Ratio Estimates and 95% Confidence Intervals

| Lens | Proportion/Odds Ratio Estimates | Alpha | Lower CL | Upper CL |
|---|---|---|---|---|
| Control | 0.752 | 0.05 | 0.665 | 0.823 |
| Test | 0.828 | 0.05 | 0.752 | 0.884 |
| Test vs. Control | 1.582 | 0.05 | 1.009 | 2.482 |

CL: Confidence Limit

We claim:

1. A contact lens that is a free radical reaction product of a reactive mixture comprising:

one or more monomers suitable for making the contact lens;

a high energy visible (HEV) light absorbing compound; and a polyamide internal wetting agent in an amount of up to eleven weight percent, wherein the contact lens transmits from 0 percent to 70 percent of light having a wavelength range of 400 to 409 nm, and wherein, in a population of wearers, wearers of the contact lens are more likely to achieve a vision break-up time of longer than 10 seconds compared to wearers of a control lens that transmits at least 90 percent of light across the wavelength range of 400 to 409 nm.

2. The contact lens of claim 1 wherein wearers of the contact lens are greater than 1.2 times more likely to achieve a vision break-up time of longer than 10 seconds compared to wearers of the control lens.

3. The contact lens of claim 1 wherein wearers of the contact lens are greater than 1.4 times more likely to achieve a vision break-up time of longer than 10 seconds compared to wearers of the control lens.

4. The contact lens of claim 1 wherein wearers of the contact lens are about 1.6 times more likely to achieve a vision break-up time of longer than 10 seconds compared to wearers of the control lens.

5. The contact lens of claim 1 wherein the reactive mixture contains less than 9 weight percent of the polyamide internal wetting agent.

6. The contact lens of claim 1 that transmits from 0.2 percent to 70 percent of light having a wavelength range of 400 to 409 nm.

7. The contact lens of claim 1 that transmits from 1 percent to 70 percent of light having a wavelength range of 400 to 409 nm.

8. The contact lens of claim 1 that transmits 45 percent or less of light having a wavelength range of 280 to 399 nm.

9. The contact lens of claim 1 that transmits at least 80 percent of light having a wavelength range of 450 to 800 nm.

10. The contact lens of claim 1 that transmits: 45 percent or less of light having a wavelength range of 280 to 399 nm; from 1 percent to 70 percent of light having a wavelength range of 400 to 409 nm; and at least 80 percent of light having a wavelength range of 450 to 800 nm.

11. The contact lens of claim 10 that transmits: from 10 percent to 95 percent of light having a wavelength range of 410 to 424 nm; and at least 50 percent of light having a wavelength range of 425 to 449 nm.

12. The contact lens of claim 11 that transmits: 20 percent or less of light having a wavelength range of 280 to 399 nm; from 3 percent to 70 percent of light having a wavelength range of 400 to 409 nm; and at least 85 percent of light having a wavelength range of 450 to 800 nm.

13. The contact lens of claim 1 wherein the monomer suitable for making the contact lens comprises a hydrophilic component, a silicone-containing component, or mixtures thereof.

* * * * *